US012678207B2

(12) United States Patent
Rush et al.

(10) Patent No.: US 12,678,207 B2
(45) Date of Patent: Jul. 14, 2026

(54) FRACTURE PLATING SYSTEMS

(71) Applicant: GLOBUS MEDICAL, INC., Audubon, PA (US)

(72) Inventors: Jesse Rush, Wayne, PA (US); Richard Scheinfield, Philadelphia, PA (US); Garret Norton, Lima, OH (US); Jessica Sandoe, Blue Bell, PA (US)

(73) Assignee: Globus Medical Inc., Audubon, PA (US)

( * ) Notice: Subject to any disclaimer, the term of this patent is extended or adjusted under 35 U.S.C. 154(b) by 126 days.

(21) Appl. No.: 18/500,259

(22) Filed: Nov. 2, 2023

(65) Prior Publication Data

US 2025/0143758 A1 May 8, 2025

(51) Int. Cl.
*A61B 17/80* (2006.01)

(52) U.S. Cl.
CPC ...... *A61B 17/8061* (2013.01); *A61B 17/8052* (2013.01)

(58) Field of Classification Search
CPC .. A61B 17/80; A61B 17/8052; A61B 17/8061
See application file for complete search history.

(56) References Cited

U.S. PATENT DOCUMENTS

| 1,105,105 A | 7/1914 | Sherman |
| 2,486,303 A | 10/1949 | Longfellow |

| 3,463,148 A | 8/1969 | Treace |
| 3,695,259 A | 10/1972 | Yost |
| 3,716,050 A | 2/1973 | Johnston |
| 4,219,015 A | 8/1980 | Steinemann |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |
| 4,781,183 A | 11/1988 | Casey et al. |
| 4,867,144 A | 9/1989 | Karas et al. |
| 4,923,471 A | 5/1990 | Morgan |
| 4,966,599 A | 10/1990 | Pollock |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,423,826 A | 6/1995 | Coates et al. |
| 5,468,242 A | 11/1995 | Reisberg |
| D365,634 S | 12/1995 | Morgan |

(Continued)

FOREIGN PATENT DOCUMENTS

| CN | 201094662 Y | 8/2008 |
| CN | 201572172 U | 9/2010 |

(Continued)

*Primary Examiner* — Si Ming Ku

(57) ABSTRACT

Devices, systems, and methods for promoting healing and stability for bone fractures. The bone stabilization system may include a variety trauma and/or reconstruction plates and one or more bone fasteners configured to secure the plate to bone. The bone plates may be used for the fixation of fractures and fragments in forefoot, midfoot, and hindfoot applications. The foot fracture plating may be used to create a rigid construct with permanent fixation to promote primary healing and stability.

4 Claims, 39 Drawing Sheets

(56)　　　　　　References Cited

U.S. PATENT DOCUMENTS

| | | | |
|---|---|---|---|
| 5,489,305 | A | 2/1996 | Morgan |
| 5,527,311 | A | 6/1996 | Procter et al. |
| 5,578,036 | A | 11/1996 | Stone et al. |
| 5,601,553 | A | 2/1997 | Trebing et al. |
| 5,676,667 | A | 10/1997 | Hausman |
| 5,690,631 | A | 11/1997 | Duncan et al. |
| 5,709,686 | A | 1/1998 | Talos et al. |
| 5,709,687 | A | 1/1998 | Pennig |
| 5,718,704 | A | 2/1998 | Medoff |
| 5,718,705 | A | 2/1998 | Sammarco |
| 5,746,742 | A | 5/1998 | Runciman et al. |
| 5,766,175 | A | 6/1998 | Martinotti |
| 5,766,176 | A | 6/1998 | Duncan |
| 5,779,706 | A | 7/1998 | Tschakaloff |
| 5,785,712 | A | 7/1998 | Runciman et al. |
| 5,797,914 | A | 8/1998 | Leibinger |
| 5,814,048 | A | 9/1998 | Morgan |
| 5,925,048 | A | 7/1999 | Ahmad et al. |
| 5,938,664 | A | 8/1999 | Winquist et al. |
| 5,961,519 | A | 10/1999 | Bruce et al. |
| 5,980,540 | A | 11/1999 | Bruce |
| 6,001,099 | A | 12/1999 | Huebner |
| 6,071,291 | A | 6/2000 | Forst et al. |
| 6,093,201 | A | 7/2000 | Cooper et al. |
| 6,096,040 | A | 8/2000 | Esser |
| 6,107,718 | A | 8/2000 | Schustek et al. |
| 6,123,709 | A * | 9/2000 | Jones ............... A61B 17/1728 |
| | | | 606/280 |
| 6,152,927 | A | 11/2000 | Farris et al. |
| 6,206,881 | B1 | 3/2001 | Frigg et al. |
| RE37,249 | E | 6/2001 | Leibinger et al. |
| 6,283,969 | B1 | 9/2001 | Grusin et al. |
| 6,309,393 | B1 | 10/2001 | Tepic et al. |
| 6,322,562 | B1 | 11/2001 | Wolter |
| 6,364,882 | B1 | 4/2002 | Orbay |
| D458,683 | S | 6/2002 | Bryant et al. |
| D458,684 | S | 6/2002 | Bryant et al. |
| D464,731 | S | 10/2002 | Bryant et al. |
| D469,532 | S | 1/2003 | Bryant et al. |
| 6,533,786 | B1 | 3/2003 | Needham et al. |
| D479,331 | S | 9/2003 | Pike et al. |
| 6,623,486 | B1 | 9/2003 | Weaver et al. |
| 6,669,700 | B1 | 12/2003 | Farris et al. |
| 6,669,701 | B2 | 12/2003 | Steiner et al. |
| 6,692,497 | B1 | 2/2004 | Tormala et al. |
| 6,712,820 | B2 | 3/2004 | Orbay |
| 6,719,759 | B2 | 4/2004 | Wagner et al. |
| 6,730,091 | B1 | 5/2004 | Pfefferle et al. |
| 6,866,665 | B2 | 3/2005 | Orbay |
| 6,955,677 | B2 | 10/2005 | Dahners |
| 6,974,461 | B1 | 12/2005 | Wolter |
| 7,001,387 | B2 | 2/2006 | Farris et al. |
| 7,063,701 | B2 | 6/2006 | Michelson |
| 7,090,676 | B2 | 8/2006 | Huebner et al. |
| 7,128,744 | B2 | 10/2006 | Weaver et al. |
| 7,137,987 | B2 | 11/2006 | Patterson et al. |
| 7,153,309 | B2 | 12/2006 | Huebner et al. |
| 7,179,260 | B2 | 2/2007 | Gerlach et al. |
| 7,250,053 | B2 | 7/2007 | Orbay |
| 7,294,130 | B2 | 11/2007 | Orbay |
| 7,322,983 | B2 | 1/2008 | Harris |
| 7,341,589 | B2 | 3/2008 | Weaver et al. |
| 7,344,538 | B2 | 3/2008 | Myerson et al. |
| 7,354,441 | B2 | 4/2008 | Frigg |
| 7,537,603 | B2 | 5/2009 | Huebner et al. |
| 7,604,657 | B2 | 10/2009 | Orbay et al. |
| 7,632,277 | B2 | 12/2009 | Woll et al. |
| 7,635,381 | B2 | 12/2009 | Orbay |
| 7,637,928 | B2 | 12/2009 | Fernandez |
| 7,655,029 | B2 | 2/2010 | Niedernberger et al. |
| 7,655,047 | B2 | 2/2010 | Swords |
| 7,695,472 | B2 | 4/2010 | Young |
| 7,717,946 | B2 | 5/2010 | Oepen et al. |
| 7,722,653 | B2 | 5/2010 | Young et al. |
| 7,740,648 | B2 | 6/2010 | Young et al. |
| D622,853 | S | 8/2010 | Raven, III |
| 7,771,457 | B2 | 8/2010 | Kay et al. |
| 7,776,076 | B2 | 8/2010 | Grady, Jr. et al. |
| 7,857,838 | B2 | 12/2010 | Orbay |
| 7,867,260 | B2 | 1/2011 | Meyer et al. |
| 7,867,261 | B2 | 1/2011 | Sixto, Jr. et al. |
| 7,875,062 | B2 | 1/2011 | Lindemann et al. |
| 7,892,264 | B2 | 2/2011 | Sanders et al. |
| 7,905,910 | B2 | 3/2011 | Gerlach et al. |
| 7,909,858 | B2 | 3/2011 | Gerlach et al. |
| 7,951,178 | B2 | 5/2011 | Jensen |
| 7,951,179 | B2 | 5/2011 | Matityahu |
| 7,976,570 | B2 | 7/2011 | Wagner et al. |
| D643,121 | S | 8/2011 | Millford et al. |
| D646,785 | S | 10/2011 | Milford |
| 8,043,297 | B2 | 10/2011 | Grady, Jr. et al. |
| 8,057,520 | B2 | 11/2011 | Ducharme et al. |
| 8,062,296 | B2 | 11/2011 | Orbay et al. |
| 8,100,953 | B2 | 1/2012 | White et al. |
| 8,105,367 | B2 | 1/2012 | Austin et al. |
| 8,114,081 | B2 | 2/2012 | Kohut et al. |
| 8,118,846 | B2 | 2/2012 | Leither et al. |
| 8,118,848 | B2 | 2/2012 | Ducharme et al. |
| 8,162,950 | B2 | 4/2012 | Digeser et al. |
| 8,167,918 | B2 | 5/2012 | Strnad et al. |
| 8,172,884 | B2 | 5/2012 | Bouman |
| 8,177,820 | B2 | 5/2012 | Anapliotis et al. |
| 8,246,661 | B2 | 8/2012 | Beutter et al. |
| 8,252,032 | B2 | 8/2012 | White et al. |
| 8,257,403 | B2 | 9/2012 | Den Hartog et al. |
| 8,257,405 | B2 | 9/2012 | Haidukewych et al. |
| 8,257,406 | B2 | 9/2012 | Kay et al. |
| 8,262,707 | B2 | 9/2012 | Huebner et al. |
| 8,267,972 | B1 | 9/2012 | Gehlert |
| 8,317,842 | B2 | 11/2012 | Graham et al. |
| 8,323,321 | B2 | 12/2012 | Gradl |
| 8,337,535 | B2 | 12/2012 | White et al. |
| 8,343,155 | B2 | 1/2013 | Fisher et al. |
| 8,382,807 | B2 | 2/2013 | Austin et al. |
| 8,394,098 | B2 | 3/2013 | Orbay et al. |
| 8,394,130 | B2 | 3/2013 | Orbay et al. |
| 8,398,685 | B2 | 3/2013 | McGarity et al. |
| 8,403,966 | B2 | 3/2013 | Ralph et al. |
| 8,419,775 | B2 | 4/2013 | Orbay et al. |
| 8,435,272 | B2 | 5/2013 | Dougherty et al. |
| 8,439,918 | B2 | 5/2013 | Gelfand |
| 8,444,679 | B2 | 5/2013 | Ralph et al. |
| 8,491,593 | B2 | 7/2013 | Prien et al. |
| 8,506,607 | B2 | 8/2013 | Eckhof et al. |
| 8,506,608 | B2 | 8/2013 | Cerynik et al. |
| 8,512,384 | B2 | 8/2013 | Beutter et al. |
| 8,512,385 | B2 | 8/2013 | White et al. |
| 8,518,090 | B2 | 8/2013 | Huebner et al. |
| 8,523,862 | B2 | 9/2013 | Murashko, Jr. |
| 8,523,919 | B2 | 9/2013 | Huebner et al. |
| 8,523,921 | B2 | 9/2013 | Horan et al. |
| 8,540,755 | B2 | 9/2013 | Whitmore |
| 8,551,095 | B2 | 10/2013 | Fritzinger et al. |
| 8,551,143 | B2 | 10/2013 | Norris et al. |
| 8,568,462 | B2 | 10/2013 | Sixto, Jr. et al. |
| 8,574,268 | B2 | 11/2013 | Chan et al. |
| 8,597,334 | B2 | 12/2013 | Mocanu |
| 8,603,147 | B2 | 12/2013 | Sixto, Jr. et al. |
| 8,617,224 | B2 | 12/2013 | Kozak et al. |
| 8,632,574 | B2 | 1/2014 | Kortenbach et al. |
| 8,641,741 | B2 | 2/2014 | Murashko, Jr. |
| 8,641,744 | B2 | 2/2014 | Weaver et al. |
| 8,663,224 | B2 | 3/2014 | Overes et al. |
| 8,728,082 | B2 | 5/2014 | Fritzinger et al. |
| 8,728,126 | B2 | 5/2014 | Steffen |
| 8,740,905 | B2 | 6/2014 | Price et al. |
| 8,747,442 | B2 | 6/2014 | Orbay et al. |
| 8,764,751 | B2 | 7/2014 | Orbay et al. |
| 8,764,808 | B2 | 7/2014 | Gonzalez-Hernandez |
| 8,777,998 | B2 | 7/2014 | Daniels et al. |
| 8,790,376 | B2 | 7/2014 | Fritzinger et al. |
| 8,790,377 | B2 | 7/2014 | Ralph et al. |
| 8,808,333 | B2 | 8/2014 | Kuster et al. |
| 8,808,334 | B2 | 8/2014 | Strnad et al. |

(56) References Cited

U.S. PATENT DOCUMENTS

| | | | |
|---|---|---|---|
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca et al. |
| 9,179,946 B2 | 11/2015 | Nehls |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,237,913 B2 | 1/2016 | Gillard et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,387 B2 | 6/2016 | Ng et al. |
| 9,370,388 B2 | 6/2016 | Globerman et al. |
| D765,850 S | 9/2016 | Early et al. |
| D765,851 S | 9/2016 | Early et al. |
| D766,437 S | 9/2016 | DaCosta |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,549,819 B1 | 1/2017 | Bravo et al. |
| 9,566,097 B2 | 2/2017 | Fierlbeck et al. |
| 9,579,133 B2 | 2/2017 | Guthlein |
| D780,924 S | 3/2017 | DaCosta |
| 9,585,706 B2 | 3/2017 | Prasad et al. |
| 9,597,130 B2 | 3/2017 | Pappalardo et al. |
| 9,597,131 B2 | 3/2017 | Price et al. |
| 9,622,799 B2 | 4/2017 | Orbay et al. |
| D785,798 S | 5/2017 | Kohler |
| 9,636,157 B2 | 5/2017 | Medoff |
| 9,649,141 B2 | 5/2017 | Raven, III et al. |
| 9,668,793 B2 | 6/2017 | Gaudin |
| 9,668,794 B2 | 6/2017 | Kuster et al. |
| 9,687,282 B2 | 6/2017 | Strnad et al. |
| 9,801,670 B2 | 10/2017 | Hashmi et al. |
| 9,814,504 B2 | 11/2017 | Ducharme et al. |
| 9,877,754 B2 | 1/2018 | Patel et al. |
| 9,888,950 B2 | 2/2018 | Perez et al. |
| 9,907,588 B2 | 3/2018 | Parekh et al. |
| 9,949,773 B2 | 4/2018 | DaCosta et al. |
| 10,064,667 B2 | 9/2018 | Leemrijse et al. |
| 10,149,708 B2 | 12/2018 | Kim et al. |
| 10,182,855 B2 | 1/2019 | Hashmi et al. |
| 10,245,085 B2 | 4/2019 | Terrill et al. |
| 10,327,824 B2 | 6/2019 | Ricker et al. |
| D855,806 S | 8/2019 | DaCosta et al. |
| 10,448,981 B2 | 10/2019 | Austin et al. |
| D874,650 S | 2/2020 | Horan et al. |
| D875,940 S | 2/2020 | DaCosta et al. |
| D891,616 S | 7/2020 | Niver et al. |
| 10,736,645 B2 | 8/2020 | McCormick |
| 10,905,477 B2 | 2/2021 | Lueth et al. |
| 11,039,865 B2 | 6/2021 | Singh et al. |
| 11,317,952 B2 | 5/2022 | Heavener et al. |
| 11,337,737 B2 | 5/2022 | Johnson et al. |
| 11,395,691 B2 | 7/2022 | Dacosta et al. |
| 11,419,647 B2 | 8/2022 | Grady, Jr. et al. |
| 11,534,212 B2 | 12/2022 | Prandi et al. |
| D977,645 S | 2/2023 | Mason et al. |
| 11,617,606 B2 | 4/2023 | Langdale et al. |
| 11,707,305 B2 | 7/2023 | Penzimer et al. |
| 2002/0045901 A1 | 4/2002 | Wagner et al. |
| 2004/0097937 A1 | 5/2004 | Pike et al. |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2006/0149265 A1 | 7/2006 | James et al. |
| 2006/0235397 A1 | 10/2006 | Sanders et al. |
| 2006/0241607 A1 | 10/2006 | Myerson et al. |
| 2006/0241608 A1 | 10/2006 | Meyerson et al. |
| 2006/0264949 A1* | 11/2006 | Kohut ............... A61B 17/8061 |
| | | 606/291 |
| 2007/0173840 A1 | 7/2007 | Huebner |
| 2007/0270849 A1 | 11/2007 | Orbay et al. |
| 2007/0288022 A1 | 12/2007 | Lutz |
| 2008/0021477 A1 | 1/2008 | Strnad et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0222047 A1 | 9/2009 | Graham |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0299369 A1 | 12/2009 | Orbay et al. |
| 2009/0312760 A1 | 12/2009 | Forstein et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0217327 A1 | 8/2010 | Vancelette et al. |
| 2010/0274247 A1 | 10/2010 | Grady, Jr. et al. |
| 2011/0092981 A1 | 4/2011 | Ng et al. |
| 2011/0106086 A1 | 5/2011 | Laird |
| 2011/0218580 A1 | 9/2011 | Schwager et al. |
| 2012/0010667 A1 | 1/2012 | Eglseder |
| 2012/0059424 A1 | 3/2012 | Epperly et al. |
| 2012/0065689 A1 | 3/2012 | Prasad et al. |
| 2012/0203227 A1 | 8/2012 | Martin |
| 2012/0232599 A1 | 9/2012 | Schoenly et al. |
| 2012/0323284 A1 | 12/2012 | Baker et al. |
| 2013/0018426 A1 | 1/2013 | Tsai et al. |
| 2013/0046347 A1 | 2/2013 | Cheng et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2013/0261675 A1 | 10/2013 | Fritzinger |
| 2013/0289630 A1 | 10/2013 | Fritzinger |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |

(56) References Cited

U.S. PATENT DOCUMENTS

| | | |
|---|---|---|
| 2014/0066998 A1 | 3/2014 | Martin |
| 2014/0094856 A1 | 4/2014 | Sinha |
| 2014/0121710 A1 | 5/2014 | Weaver et al. |
| 2014/0148859 A1 | 5/2014 | Taylor et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0330320 A1 | 11/2014 | Wolter |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0066094 A1 | 3/2015 | Prandi et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0327899 A1* | 11/2015 | Early ............... A61B 17/8061 |
| | | 606/280 |
| 2015/0335365 A1 | 11/2015 | Neufeld et al. |
| 2015/0351816 A1 | 12/2015 | Lewis et al. |
| 2015/0374421 A1 | 12/2015 | Rocci et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0051299 A1* | 2/2016 | Price ................. A61B 17/1728 |
| | | 606/281 |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0183990 A1 | 6/2016 | Koizumi et al. |
| 2016/0262814 A1 | 9/2016 | Wainscott |
| 2016/0278828 A1 | 9/2016 | Ragghianti |
| 2016/0310183 A1 | 10/2016 | Shah et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0105775 A1 | 4/2017 | Ricker et al. |
| 2017/0215931 A1 | 8/2017 | Cremer et al. |
| 2018/0153597 A1 | 6/2018 | Early et al. |
| 2019/0269446 A1* | 9/2019 | Laird, Jr. ........... A61B 17/8061 |
| 2021/0282823 A1 | 9/2021 | Day et al. |
| 2022/0061861 A1 | 3/2022 | Coyne et al. |
| 2022/0226028 A1 | 7/2022 | Dayton et al. |
| 2022/0273348 A1 | 9/2022 | Schaefer et al. |
| 2023/0057743 A1 | 2/2023 | Niver et al. |
| 2023/0104559 A1 | 4/2023 | Cowan et al. |

FOREIGN PATENT DOCUMENTS

| | | |
|---|---|---|
| CN | 201987653 U | 9/2011 |
| CN | 202313691 U | 7/2012 |
| CN | 202821574 U | 3/2013 |
| CN | 202821575 U | 3/2013 |
| CN | 203506858 U | 4/2014 |
| CN | 203576620 U | 5/2014 |
| CN | 103919600 A | 7/2014 |
| CN | 203815563 U | 9/2014 |
| CN | 204033469 U | 12/2014 |
| CN | 104367376 A | 2/2015 |
| CN | 104546102 A | 4/2015 |
| CN | 204410950 U | 6/2015 |
| CN | 204446081 U | 7/2015 |
| CN | 105213012 A | 1/2016 |
| CN | 105982727 A | 10/2016 |
| CN | 206896399 U | 1/2018 |
| CN | 108210052 A | 6/2018 |
| CN | 108836460 A | 11/2018 |
| CN | 208319299 U | 1/2019 |
| CN | 208525022 U | 2/2019 |
| CN | 208910446 U | 5/2019 |
| CN | 109833085 A | 6/2019 |
| CN | 110215268 A | 9/2019 |
| CN | 111529042 A | 8/2020 |
| CN | 211355824 U | 8/2020 |
| CN | 211433249 U | 9/2020 |
| CN | 213129834 U | 5/2021 |
| CN | 213641141 U | 7/2021 |
| CN | 113303895 A | 8/2021 |
| CN | 114081607 A | 2/2022 |
| CN | 215874902 U | 2/2022 |
| CN | 114145831 A | 3/2022 |
| CN | 217338793 U | 9/2022 |
| CN | 217472053 U | 9/2022 |
| CN | 218305086 U | 1/2023 |
| CN | 219480303 U | 8/2023 |
| DE | 202007002190 U1 | 5/2007 |
| DE | 202009008872 U1 | 10/2009 |
| DE | 102011017033 A1 | 4/2012 |
| EP | 1121903 A2 | 8/2001 |
| FR | 2622431 A1 | 5/1989 |
| FR | 2846870 A1 | 5/2004 |
| FR | 2928259 A1 | 9/2009 |
| JP | 2003210478 A | 7/2003 |
| JP | 2006280947 A | 10/2006 |
| JP | 2018149297 A | 9/2018 |
| JP | 2018531137 A | 10/2018 |
| TW | 201316942 A | 5/2013 |
| WO | 0139680 A1 | 6/2001 |
| WO | 20041024009 A1 | 3/2004 |
| WO | 2016079504 A1 | 5/2016 |
| WO | 2018/085365 A3 | 5/2018 |
| WO | 2020168058 A1 | 8/2020 |

* cited by examiner

12

(a)    (b)    (c)    (d)

14

16

18

4

300

4

500

4

4

700

4

800

800

810  16  806
16  802
16
16  810
16
16  808
14
804  810
16

4

900

900

910  16
902    906
16
910
16    908
910
904
910  16

4

1300'

1300'

1302

18

16

16

16

16

16

1308

1306

18

1304

1312

1310

16

4

1400

1400

18

16

16

1402

1404

1410

1408

16

16

1406

4

1400'

10'

(a)    (b)        (c)                    (d)

(e)    (f)

(g)        (h)        (i)

4

1500'

4

1700

4

FRACTURE PLATING SYSTEMS

FIELD OF THE INVENTION

The present disclosure relates to surgical devices, and more particularly, to stabilization systems, for example, for trauma applications.

BACKGROUND OF THE INVENTION

Trauma plates are orthopedic devices used to stabilize and fixate fractures in the bones. For fractures of the foot, specialized plates may be used to address fractures and fragmentations in the foot to ensure proper alignment and facilitating healing. The foot and ankle have over 25 bones and 33 joints. The foot can be split into three main regions: forefoot, midfoot, and hindfoot. These parts work together with the ankle, to provide the body with support, balance, and mobility. The forefoot region may include fractures in the metatarsals and phalanges. The midfoot region may include fractures of the tarsals including the navicular, cuboid, and cuneiforms. The hindfoot region may include fractures in the tarsals including the talus and calcaneus (heel bone). For fractures of bones with complex fractures or complex three-dimensional geometry, reconstruction plates may be used for corrections and bone stabilization. A variety of plates may be used to help treat fractures and broken segments in different areas of the body. There remains a need, however, for improved plate styles and plating systems that can treat a vast array of fracture patterns and accommodate multiple deformities.

SUMMARY OF THE INVENTION

To meet this and other needs, and in view of its purposes, the present application provides devices, systems, and methods for promoting healing and stability for bone fractures. In particular, the plates may include a comprehensive offering of plate styles able to treat a vast array of fracture patterns. The plates are capable of being used for both definitive, permanent fixation, as well as temporary or supplemental fixation in accordance with other systems. The specific plate styles afford the ability to accommodate multiple fracture patterns. The plates are capable of being cut and contoured to accommodate extreme patient anatomy. The large range of screw and plate sizes can accommodate multiple anatomies and anatomic regions.

According to one embodiment, a bone stabilization system includes a collection of bone plates configured for stabilization of a fracture, dislocation, or reconstruction of a deformity. Each bone plate is configured to be positioned against an exterior surface of a bone in the forefoot, midfoot, and/or hindfoot. The system includes one or more fasteners, such as locking and/or non-locking bone screws that a surgeon may select based on preference for a specific anatomical case. The locking fasteners may connect to the plate and the bone to thereby lock the plate to the bone. The non-locking fasteners may be able to dynamically compress the bone and create interfragmental and/or joint compression. The plate may include one or more K-wire holes or slots to help guide and temporarily hold the plates in position.

According to one embodiment, a bone stabilization plate includes a 5$^{th}$ metatarsal hook plate with a body extending from a first proximal end configured to sit on the tuberosity of the 5$^{th}$ metatarsal to a second distal end configured to sit on the body of the 5$^{th}$ metatarsal. The plate includes a curved proximal hook configured to grasp or anchor into the tuberosity of the 5$^{th}$ metatarsal. The hook may terminate with two parallel curved prongs having sharp pointed tips. Alternatively, the bone stabilization plate is a 5$^{th}$ metatarsal tab plate where the hook is replaced with a curved tab.

According to one embodiment, a bone stabilization plate includes a coupled Lisfranc 1$^{st}$ & 2$^{nd}$ tarsometatarsal plate. The coupled plate has a bifurcated body that extends from a first proximal end configured to sit on the medial and intermediate cuneiforms to a second distal end configured to sit on the bodies of the 1$^{st}$ and 2$^{nd}$ metatarsals, respectively. The coupled plate includes first and second legs connected by a proximal crossbeam and a bridge that links the two legs of the plate together for added strength. Alternatively, the bone stabilization plate is a coupled Lisfranc 2$^{nd}$ & 3$^{rd}$ tarsometatarsal plate where the proximal end is configured to sit on the intermediate and lateral cuneiforms and the distal end is configured to sit on the bodies of the 2$^{nd}$ and 3$^{rd}$ metatarsals, respectively.

According to one embodiment, a bone stabilization plate includes a flower plate configured to sit dorsally on the cuboid bone. The flower plate may have petal-like or lobe-like extensions radiating outward from a central circular region. Each lobe and the central region may define a polyaxial hole for receiving respective locking fasteners, thereby securing the flower plate to the bone.

According to one embodiment, a bone stabilization plate includes a utility plate with an H-shaped body where one end sits on the navicular bone and the other end sits on the cuneiform bone, for example. The H shape may be formed by four lobes or tabs defining the four corners of the H shape. A dynamic compression slot may be aligned along a central axis to provide compression to the bone fragment(s) and/or the joint. Alternatively, an H-plate may be used to fix or fuse the navicular-cuneiform joint, the talo-navicular joint, the calcaneocuboid joint, the tarso-metatarsal joint, or other joints or bone fractures.

According to one embodiment, a bone stabilization plate includes a sinus tarsi wave plate, a sinus tarsi tongue plate, or a rafting perimeter plate. The plate may have an elongate body having a top surface and an opposite, bottom surface configured to contact bone. The elongate body may have a first section, a main body, and a second section. The elongate body defines a plurality of screw holes therethrough. The first section is offset from the main body with two tabs. The main body includes a three-hole polyaxial cluster where an axis of each hole is located at vertices of an equilateral triangle. The second section includes a series of polyaxial holes following a wave pattern.

The bone stabilization plate may include one or more of the following features. The plate may be contoured to sit laterally on a calcaneus below a talus. The two tabs may be angled inward and toward one another toward the main body. The elongate body may define a K-wire hole having a diameter smaller than the diameter of each of the screw holes. The elongate body may include a posterior extension including a straight continuation of the second section. The posterior extension may include a linear arrangement of polyaxial holes. The elongate body may include a plantar offset extension extending from the second section. The plantar offset extension may include a second straight continuation of the second section angled relative to the posterior extension. The plantar offset extension may include a solid linear body that terminates with a three-hole cluster. The plantar offset extension may be connected to the posterior extension by a cross member. The main body may be connected to the planar offset extension by a rear extension.

According to one embodiment, a bone stabilization plate may include a calcaneus perimeter plate. The plate includes a body having a top surface and an opposite, bottom surface configured to contact bone. The body has a plurality of rings defining screw holes therethrough. The rings are connected together via struts forming a lattice structure with one or more through spaces remaining between the connections. A perimeter of rings may be linked together with perimeter struts and one or more inner rings and inner struts may provide cross-bracing to the plate. The plate may include a cuboid plate, navicular plate, or a calcaneus plate, for example.

The bone stabilization plate may include one or more of the following features. The perimeter of rings and perimeter struts may align with a calcaneus. Each ring may connect to another ring with one strut. The inner rings may connect to more than one perimeter ring. A bottom portion of the plate may define a series of perimeter rings and perimeter struts arranged in a straight line. One end of the plate may form a quadrilateral shape, and the opposite end of the plate may form a rounded shape larger than the quadrilateral shape.

According to one embodiment, a bone system includes a bone plate and a plurality of bone fasteners. The bone plate has a top surface and an opposite, bottom surface configured to contact bone. The bone plate defines a plurality of polyaxial screw holes therethrough. The screw holes include a three-hole polyaxial cluster where an axis of each hole is located at vertices of an equilateral triangle. The plurality of bone fasteners is configured to lock in the polyaxial screw holes.

The bone stabilization system may include one or more of the following features. The bone plate may define a compression slot configured to receive a non-locking fastener for applying compression. The bone plate may define a K-wire slot configured to achieve further compression with a K-wire. The bone plate may include one or more markings to indicate a location of a joint.

According to one embodiment, a bone stabilization plate includes a talus T-plate contoured to sit laterally on the neck of the talus. The talus T-plate may have a body with a substantially T-shaped profile with an elongate posterior leg and a transverse anterior cross-portion. Alternatively, the plate may include a L-plate where one wing or extension of the cross-portion has been removed.

According to one embodiment, a bone stabilization plate includes a talus butterfly plate contoured to sit laterally on the neck of the talus. The talus butterfly plate may have a symmetrical butterfly-like shape with opposed wings. The wings may include lobes defining each polyaxial hole. Alternatively, a large talus butterfly plate may extend the wings or lobes to additional holes for fixation.

According to one embodiment, a bone stabilization plate includes a metatarsophalangeal (MTP) plate contoured to sit on the dorsal aspect of the first MTP joint. The plate may have an elongate body extending from a first end to a second end along a central longitudinal axis. The plate includes a straight bridge section configured to extend over the MTP joint. A compression slot and a K-wire slot may be aligned along the central longitudinal axis to apply compression to the bone fragments and/or the joint. Alternatively, the plate is a narrow MTP plate with less distal screw holes for a lower profile on the phalanx.

According to one embodiment, a bone stabilization plate includes a ladipus plate contoured to sit on the medial aspect of the $1^{st}$ tarsometatarsal (TMT) joint. The plate may be angled with a bridge section configured to span the joint. The lapidus plate may include four poly-axial locking holes, two for the metatarsal and two for the cuneiform, with one compression slot on the side of the metatarsal.

According to one embodiment, a bone stabilization plate includes a tarsometatarsal (TMT) plate that extends from a first proximal end configured to sit on the cuneiform to a second distal end configured to sit on the metatarsal. The distal section of the plate may include two or four poly-axial holes with a compression slot aligned along the central longitudinal axis to provide compression to the joint.

According to one embodiment, a bone stabilization plate includes a navicular-cuneiform (NC) plate configured to stabilize the medial and middle cuneiform to the navicular and also allow for an interfragmentary screw to be positioned through a sunken hole in the plate. The sunken hole may be located along the central axis of the plate but the hole axis may be angled such that the lag screw inserts distally.

According to one embodiment, a bone stabilization plate includes a medial column plate configured to bridge across the midfoot covering the talus, navicular, medial cuneiform, and first metatarsal. The plate may have an elongate body with four sections, a proximal talus section, a navicular section, a cuneiform section, and a distal metatarsal section, extending along a central longitudinal axis. Each section includes a cluster of polyaxial holes for receiving locking bone fasteners into the respective bones. A pair of K-wire slots may be aligned along the central longitudinal axis to provide compression to the bone fragments and/or joints.

According to one embodiment, a bone stabilization plate includes an Evans osteotomy wedge plate configured to fit into a calcaneal osteotomy. The plate may have symmetrical dog bone-like shape and the wedge may include inclined planes or surfaces configured to spread the bone at an angle, for example, for lateral column lengthening of a flatfoot deformity.

According to one embodiment, a bone stabilization plate includes a Cotton opening wedge plate configured to fit into a medial cuneiform osteotomy. The plate may have a symmetrical shape with four lobes and the wedge may include inclined planes or surfaces configured to spread the bone at an angle, for example, to help create an arch in the foot.

According to one embodiment, a bone stabilization plate includes a calcaneal slide plate configured to fixate a calcaneus osteotomy. The plate may include a plate portion with lobes defining polyaxial holes and a wedge portion defining polyaxial holes, which allow for two polyaxial fasteners to be placed on either side of the osteotomy.

According to one embodiment, a method of stabilizing a bone fracture includes one or more of the following steps in any suitable order: (1) positioning a bone plate against an exterior surface of one or more bones of the foot; (2) optionally, applying compression via a compression slot or K-wire slot to the bone fragments and/or joint(s); and (3) securing the bone plate to the bone by attaching a first set of fasteners through the bone plate in one bone or bone fragment and attaching a second set of fasteners through the bone plate in another bone or bone fragment. The plate may be configured to extend across one or more fractures and/or joints in the foot.

Also provided are kits for the stabilization systems including bone plates of varying types and sizes, fasteners of varying types and sizes including locking fasteners, non-locking fasteners, compression fasteners, polyaxial fasteners, fixed angle fasteners, or any other suitable fasteners, drill guides, K-wires, sutures, and other components for installing the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Embodiments of the disclosure are generally directed to devices, systems, and methods for promoting healing and stability for bone fractures. The plates may include a comprehensive offering of plate styles for stabilization of a fracture, dislocation, or reconstruction of a deformity. The bone plates may be used to create a very rigid construct with permanent fixation to promote primary healing and stability. Alternatively, the plates are also capable of being used as temporary or supplemental fixation.

A series of trauma and/or reconstruction plates may be used for the fixation of fractures and fragments in forefoot, midfoot, and hindfoot applications. The foot fracture plates may be used to address fractures and fragmentations in the foot to ensure proper alignment and facilitating healing. The foot includes three main anatomical regions: the forefoot, the midfoot, and the hindfoot.

The forefoot includes the five toes also known as phalanges and their connecting long bones or metatarsals. Several small bones together from one phalanx or toe. Four of the five toes have three phalanx bones respectively connected by two joints. The big toe or hallux has two phalanx bones distal and proximal with a joint in between called the interphalangeal joint. The big toe articulates with the head of the first metatarsal at the first metatarsophalangeal (MTP) joint and there are two sesamoids on the plantar side of the metatarsal head. The phalanges are connected to the metatarsals at the ball of the foot. The forefoot balances pressure on the ball of the foot and bears a substantial amount of the body weight.

The bones of the midfoot from medial to lateral are the $1^{st}$ through $3^{rd}$ cuneiform, the cuboid, and the crescent-shaped navicular bone posterior to the cuneiforms. The navicular articulates with the talus, establishing the foundation for the ankle joint where the tibia, fibula, and foot converge in a hinged connection. The five tarsal bones of the midfoot act together to form a lateral arch and a longitudinal arch which help to absorb shock.

The hindfoot, the most posterior aspect of the foot, includes three joints, which link the midfoot to the ankle: subtalar, calcaneocuboid, and talonavicular. The calcaneus, also known as the heel bone, is found at the back of the foot near the ankle, just below the talus, tibia, and fibula bones of the lower leg. The calcaneus is joined to the talus at the subtalar joint, which allows for rotation of the foot.

Figure 1:
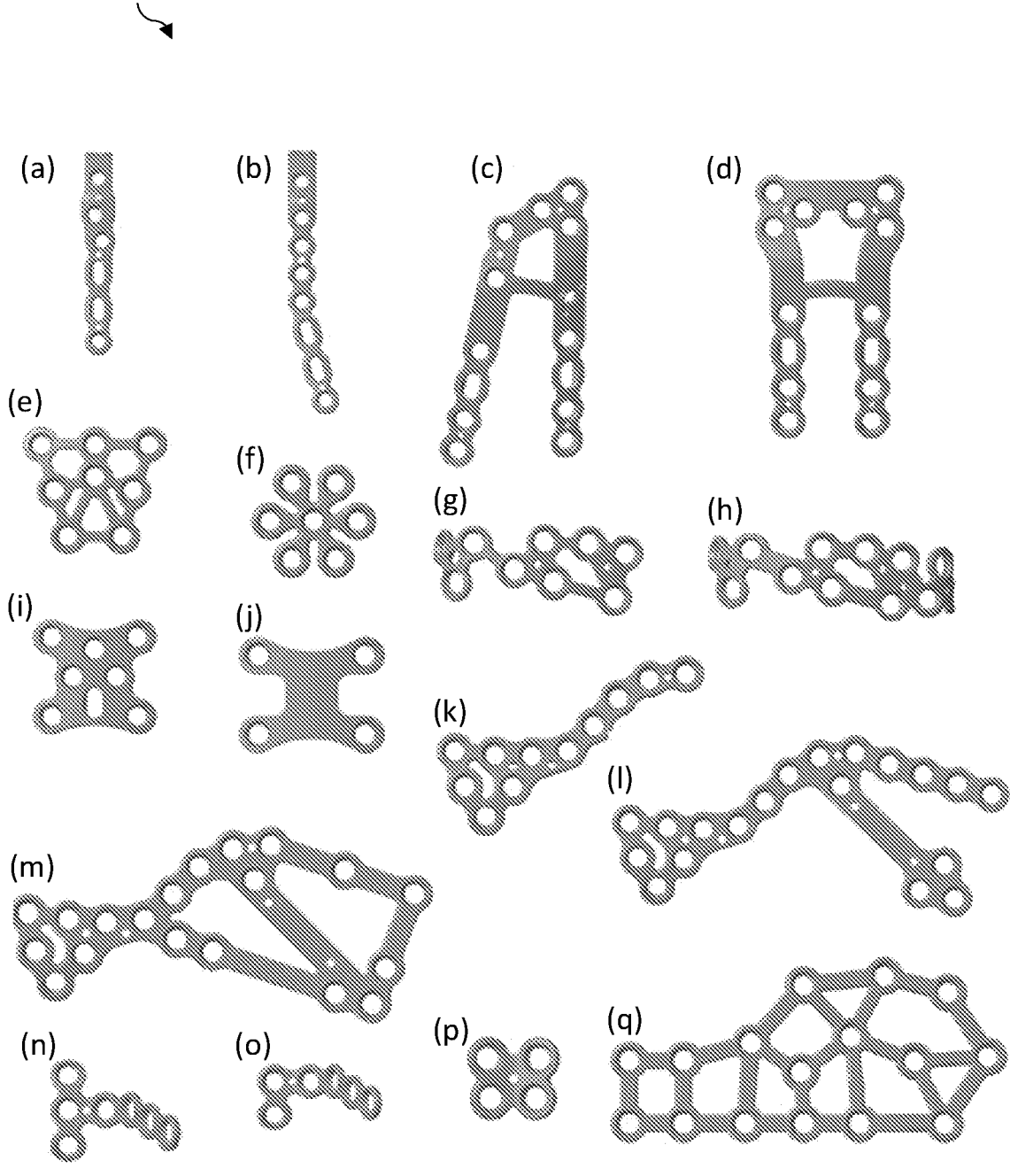
FIG. 1 shows a collection of plate styles configured for fixation of fractures and fragments in the forefoot, midfoot, and hindfoot.

Referring now to FIG. 1, a collection of plate styles 10 configured for fixation of fractures and fragments in the forefoot, midfoot, and hindfoot is shown. Seventeen different foot plate styles may be used in the treatment of various fractures of the foot including: (a) $5^{th}$ metatarsal hook plates; (b) $5^{th}$ metatarsal tab plates; (c) coupled Lisfranc $1^{st}$ & $2^{nd}$ tarsometatarsal plates; (d) coupled Lisfranc $2^{nd}$ & $3^{rd}$ tarsometatarsal plates; (e) cuboid plates; (f) flower plates; (g) navicular plates; (h) navicular plates with plantar bundle; (i) utility plates; (j) H-plates; (k) sinus tarsi wave plates; (l) sinus tarsi tongue type plates; (m) rafting perimeter plates; (n) talus T-plates; (o) talus L-plates; (p) talus butterfly plates; and (q) perimeter calcaneus plates.

Each bone plate 10 is configured to be positioned against an outside face of a bone and/or joint, for example, of the foot. The bone plate 10 spans the bone fracture(s) and/or joints to hold the bone fragments together, allowing the bone to heal in the correct alignment. These plates 10 may be provided in a number of variations in a surgical tray, which include for example various types, sizes, and configurations. The tray selection may allow for the surgeon to select a desired plate during surgery after opening the wound area and considering the plating needs for the patient. Although the collection of plates 10 is generally described with reference to stabilizing the foot, it will be appreciated that the stabilization systems described herein may be used or adapted to be used for the fixation of other areas or other bones as well including the femur, tibia, humerus, clavicle, fibula, ulna, radius, bones of the hand, or other suitable bone(s) or joint(s). The bone plates 10 may be available in a variety of lengths, widths, and styles based on the anatomy of the patient and types of fractures. The systems may be adapted to secure small or large bone fragments, single or multiple bone fragments, or otherwise secure one or more fractures or joints.

Figure 2:
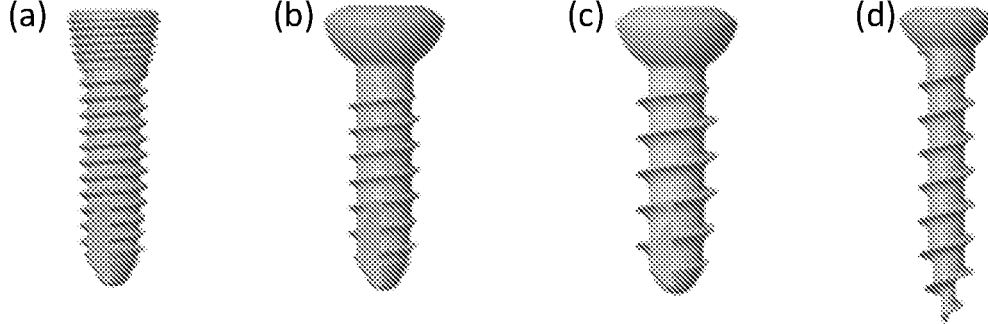
FIG. 2 shows a series of screw styles configured to secure the fracture plates to bone.

Turning now to FIG. 2, four different screw types 12 capable of being used with or without plates 10 in the treatment of various fractures are shown, including: (a) locking screws; (b) non-locking screws; (c) cancellous screws; and (d) speed screws. Each plate 10 may be configured to receive one or more of the bone fasteners or screws 12. The screws 12 may be configured to pass through the plate 10 and into the bone, thereby securing the plate 10 to the bone. Although screws are exemplified, the fasteners 12 may also include other fasteners or anchors configured to be secured or engaged with bone, such as nails, spikes, staples, pegs, barbs, hooks, or the like. The fasteners 12 may be cannulated such that they may be guided into place over guide wires or K-wires.

Each screw 12 may include a head portion configured to engage the plate and a threaded shaft portion configured to engage bone. The screws 12 may come in locking and non-locking options. In the case of screw type (a) locking screws, the head portion may include threads or a textured area configured to lock the screw 12 to the plate 10. In the case of screw type (b) non-locking screws, the head portion may be substantially rounded and smooth to allow for dynamic compression of the bone. In the case of screw type (c) cancellous screws, the screws 12 are non-locking screws designed for insertion into cancellous bone. The cancellous screws may have a wider thread than cortical screws to allow for better purchase in the softer, spongy bone. In the case of screw type (d) speed screws, the screws may have a sharp self-drilling tip with a narrower shaft diameter designed for fast insertion. The plates 10 may be configured to accept multiple screw sizes representing the outer diameter of the threads of the screws offered in each screw type (e.g., 2.0 mm, 2.5 mm, 3.0 mm). In some cases, the screw may be a hybrid screw that has one major diameter on the threads (e.g., 3.0 mm) but a head size that matches another diameter (e.g., 2.5 mm). This provides surgeons with a larger selection of screw options to use and may also serve as a bail out option.

Figure 3:
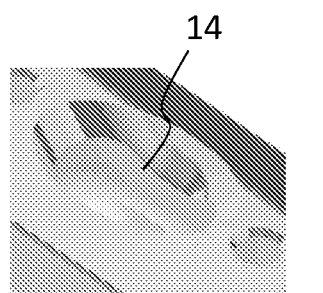
FIG. 3 shows several hole types available in one or more of the fracture plates.
Figure 3:
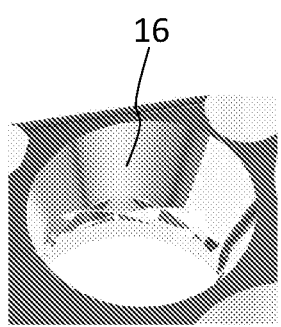
Figure 3:
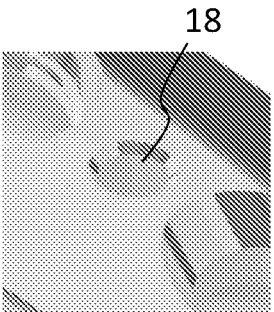

Turning now to FIG. 3, the plates 10 may include one or more openings or hole types 14, 16, 18, 20. The fastener openings 14, 16 may include cylindrical openings, conical openings, elongated openings, threaded openings, textured openings, non-threaded and/or non-textured openings, and the like. The openings 14, 16 extending through the plate 10 are configured to accept locking fasteners, non-locking fasteners, or a combination of both locking and non-locking fasteners that are able to dynamically compress the bone and/or affix the plate 10 to the bone. For example, a first opening type may include an elongated opening or dynamic compression slot 14, which allows for static insertion of non-locking screws 12 into the bone and/or compression (e.g., between 0.5-2 mm, such as 1 mm of compression) along the bone through eccentric insertion of the non-locking screw 12. A second opening type may include a polyaxial locking hole 16 with a textured portion configured to engage a head portion of the locking fastener. The locking screw 12 may include threads or a textured area configured to deform and/or engage with the locking hole 16, thereby locking the fastener 12 to the plate 10. A third opening type may include a K-wire hole 18, which is configured to receive a guide wire of K-wire therethrough. A fourth opening type may include an elongated K-wire slot 20, which allows for compression with a guide wire or K-wire. Additional details on these and other types of openings are provided in further detail in U.S. Pat. No. 11,432,857, which is incorporated by reference herein in its entirety for all purposes. The plate 10 may comprise any suitable number of openings 14, 16, 18, 20 in any suitable configuration. These openings allow surgeons flexibility for fastener placement based on preference, anatomy, and fracture location. Surgeons may have differing opinions as to the number, location, and types of fasteners 12. The complexity of fracture location and shape may make it desirable to have as many fastener locations as possible to treat the fracture(s).

The bone plate 10 may be comprised of titanium, stainless steel, cobalt chrome, carbon composite, plastic or polymer-such as polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the fasteners 12 may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates and bone fasteners are made, it should be understood that bone plates and fasteners comprised of any appropriate material are contemplated.

Figure 4A:
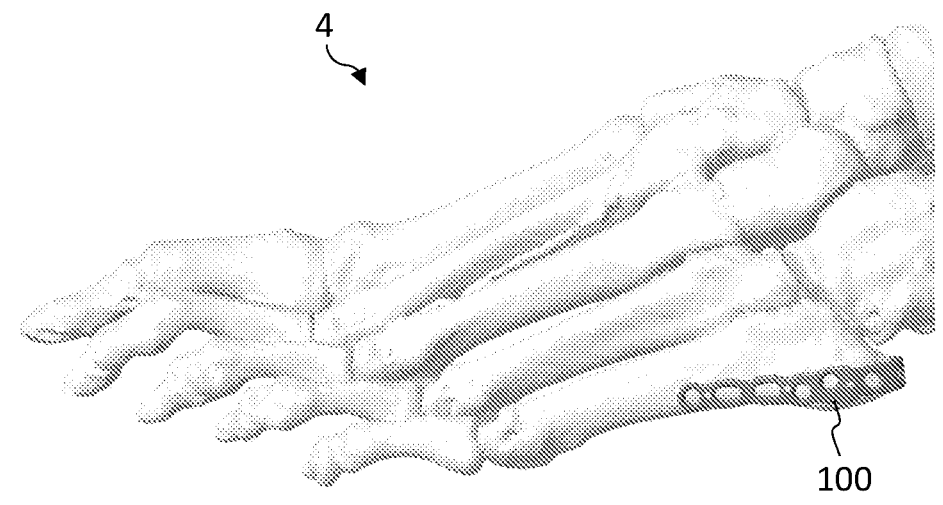
FIGS. 4A-4D depict a fifth metatarsal hook plate sitting on the lateral aspect of the fifth metatarsal according to one embodiment.
Figure 4B:
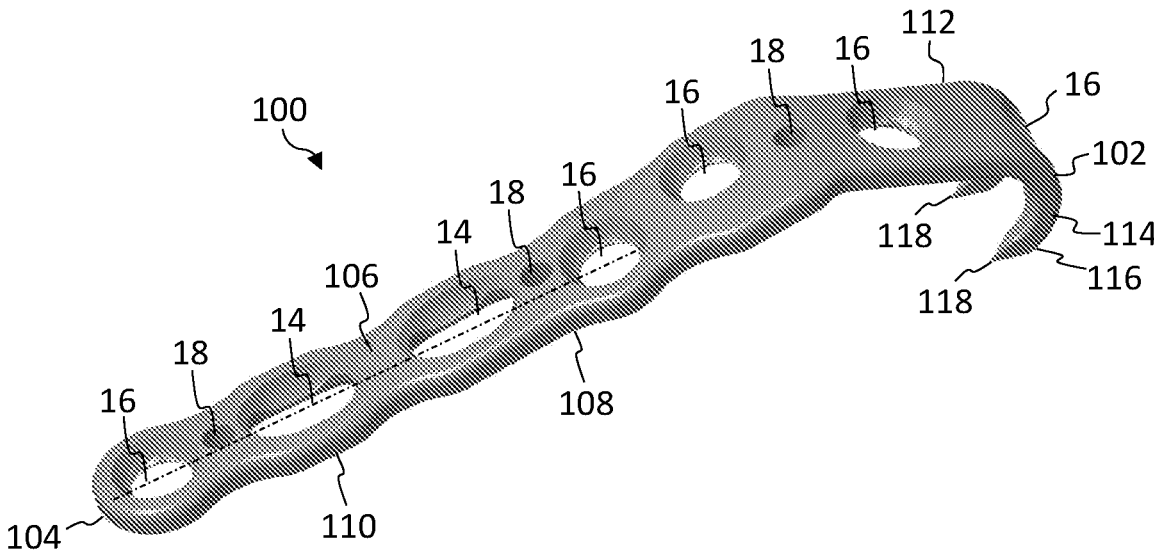

Turning now to FIGS. 4A-4D, a $5^{th}$ metatarsal hook plate 100 is shown according to one embodiment. FIG. 4A depicts the anatomy of the foot 4 with the $5^{th}$ metatarsal hook plate 100 contoured to sit on the lateral aspect of the base of the $5^{th}$ metatarsal. The hook plate 100 has a body that extends from a first end or proximal end 102 configured to sit on the tuberosity of the $5^{th}$ metatarsal to a second end or distal end 104 configured to sit on the body of the $5^{th}$ metatarsal. The plate 100 includes a top surface 106 and an opposite, bottom surface 108 configured to contact adjacent bone. The top and bottom surfaces 106, 108 are connected by opposite side surfaces extending from the first to second ends 102, 104 of the plate 100. The plate 100 may be separated into three sections: distal portion 110, bent portion 112, and proximal hook 114. The distal portion 110 may have an elongated longitudinal body with a generally flat profile. The bent portion 112 may be angled relative to the distal portion 110 and the proximal hook 114 may extend from the bent portion 112. Although one version of plate 100 is shown, it will be appreciated that any suitable shape and contouring of the plate 100 may be provided depending on the location and type of fracture to be plated.

Figure 4C:
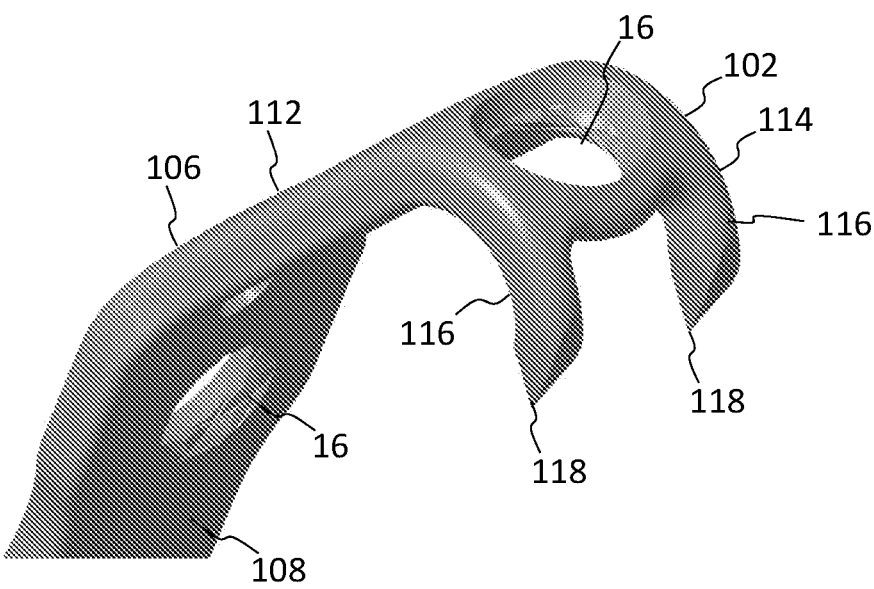

With further emphasis on FIG. 4C, the proximal end 102 of the plate 100 extends into a pronounced curved hook 114 configured to grasp or anchor into the tuberosity of the $5^{th}$ metatarsal. The proximal hook 114 may define a dual hook end that terminates as a pair of distinct curved prongs 116 with sharpened points or pointed ends 118. The curved prongs 116 may be separated from one another by a gap or interspace. The pair of prongs 116 may be aligned in parallel or otherwise configured. The curved hook 114 and prongs 116 may curve downward in an arc or crescent shape such that the pointed ends 118 point back toward the distal end 104. The hook 114 may be used to capture an avulsion fracture or a Jones fracture at the base of the $5^{th}$ metatarsal.

The hook plates 100 may comprise any suitable number and type of openings 14, 16, 18 in any suitable configuration. In the embodiment shown, a number of polyaxial locking holes 16 are positioned along the body of the plate 100. For example, one polyaxial hole 16 may be positioned near the distal end 104 and several polyaxial holes 16 are located toward the proximal end 102. One polyaxial hole 16 may be defined through the curved hook 114 and adjacent to the prongs 116. The curvature of hook 114 allows for a different orientation of screw insertion. In particular, the hole axis of polyaxial hole 16 defined into the hook 114 may be aligned and configured to place a screw 12 intramedullary through the canal of the $5^{th}$ metatarsal. The remaining polyaxial holes 16 may be used to fixate the plate 100 to the bone. Three K-wire holes 18 are provided along the length of the plate 100. The K-wire holes 18 offer additional points of fixation for the plate 100. Driving K-wires through the appropriate holes 18 in the plate 100 allows the plate 100 to be held on the bone while adjacent bone screws 12 can be inserted through the polyaxial holes 16.

Figure 4D:
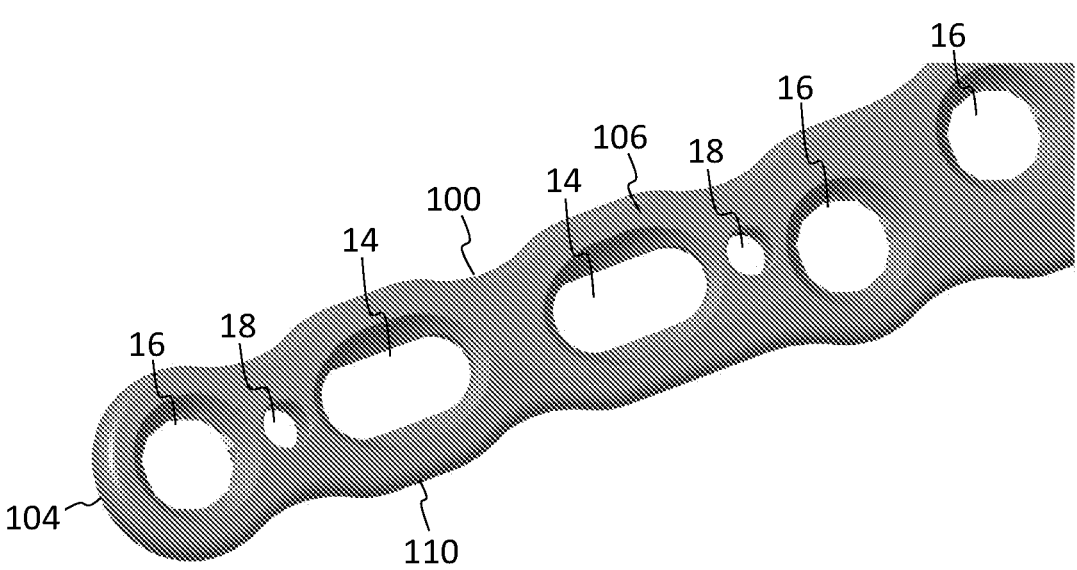

As best seen in FIG. 4D, the plate 100 may define two dynamic compression slots 14 towards the distal end 104. The dynamic compression slots 14 may be aligned with a central axis of the implant 100 and located between opposite K-wire holes 18. The dynamic compression slots 14 of the plate 100 may help with compression of an avulsion fracture or a Jones fracture of the $5^{th}$ metatarsal. The outer edges of the plate 100 may be scalloped or wavy to follow the hole pattern, minimizing potential soft tissue irritation. The $5^{th}$ metatarsal hook plates 100 may be offered in small and large sizes as well as left and right configurations. Large plates may feature a slight bend distally to match the curvature of the $5^{th}$ metatarsal.

Figure 5A:
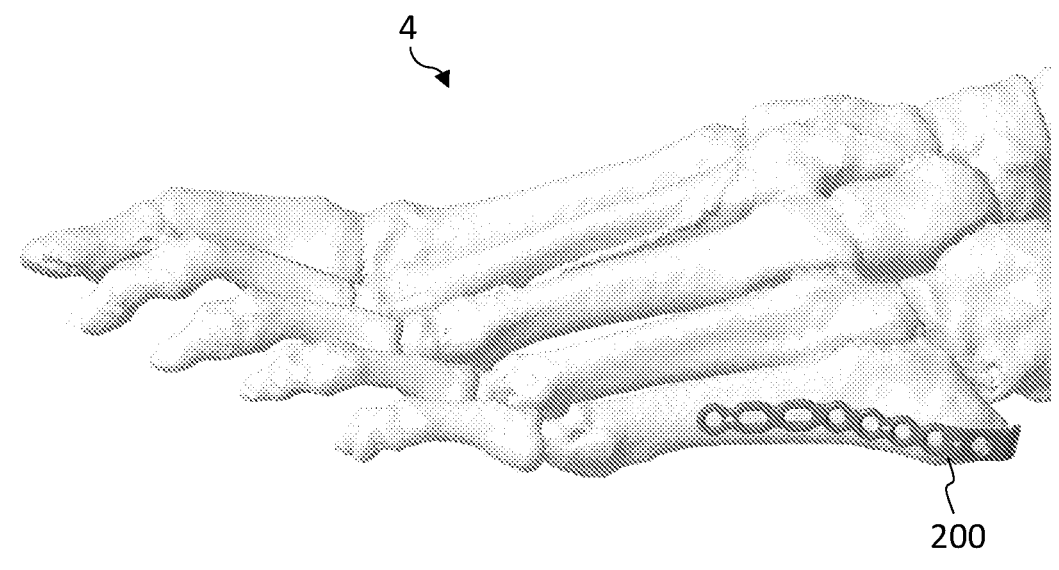
FIGS. 5A-5C depict a fifth metatarsal tab plate sitting on the lateral aspect of the fifth metatarsal according to one embodiment.
Figure 5B:
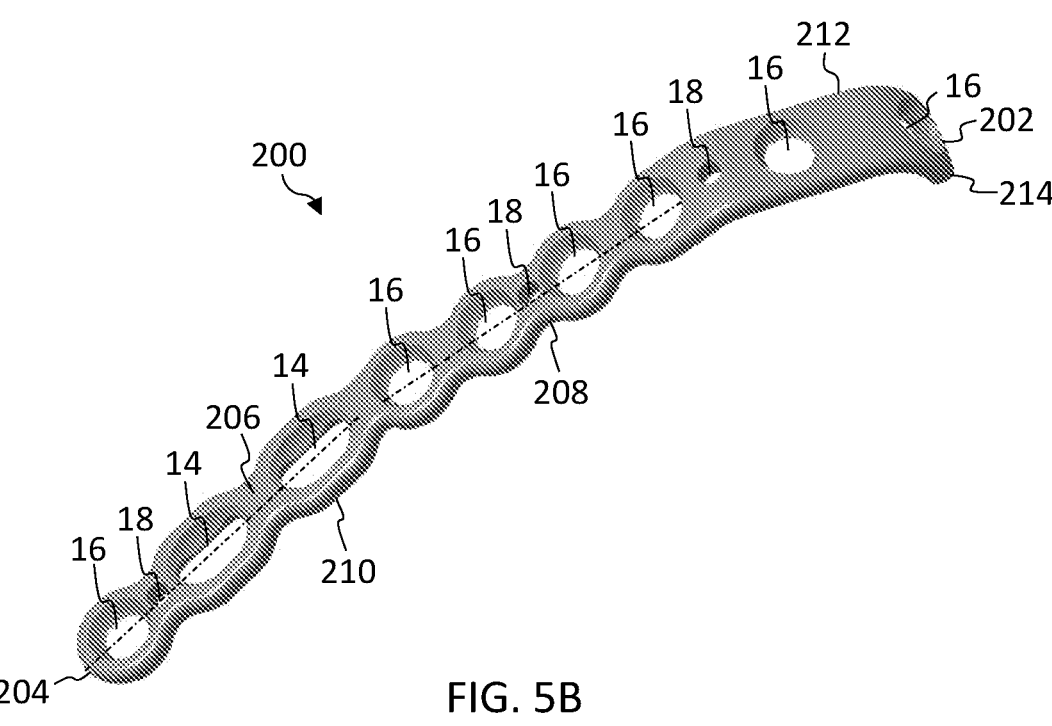
Figure 5C:
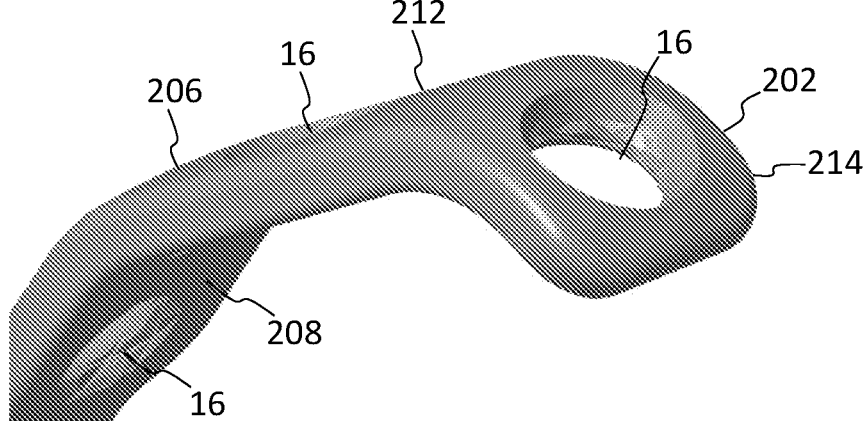

Turning now to FIGS. 5A-5C, a $5^{th}$ metatarsal tab plate 200 is shown according to one embodiment. The tab plate 200 is similar to hook plate 100 except a curved tab 214 replaces the curved hook and prongs on the proximal end. FIG. 5A depicts the anatomy of the foot 4 with the $5^{th}$ metatarsal tab plate 200 contoured identically to the $5^{th}$ metatarsal hook plate 100 to sit on the base of the lateral aspect of the $5^{th}$ metatarsal. The tab plate 200 extends from proximal end 202 configured to sit on the tuberosity of the $5^{th}$ metatarsal to the distal end 204 configured to sit on the body of the $5^{th}$ metatarsal. The plate 200 includes top surface 206 and bottom surface 208 with openings 14, 16, 18 extending therethrough. The plate 200 may include distal portion 210, bent portion 212, and proximal tab 214. With further emphasis on FIG. 5C, the proximal end 202 of the plate 200 includes curved tab 214 configured to grasp or anchor into the tuberosity of the $5^{th}$ metatarsal. The curved tab 214 may curve into an arc or crescent shape. The curved tab 214 may be used to capture an avulsion fracture or a Jones fracture at the base of the $5^{th}$ metatarsal. One polyaxial hole 16 may be defined through the curved tab 214. The curvature of tab 214 allows for a different orientation of screw insertion. In particular, the hole axis of polyaxial hole 16 defined into the tab 214 may be aligned and configured to place a screw 12 intramedullary through the canal of the $5^{th}$ metatarsal. The tab plates 200 may be offered in small and large sizes as well as left and right configurations.

Figure 6A:
FIGS. 6A-6E depict a coupled Lisfranc first and second tarsometatarsal plate sitting on the dorsal aspect of the medial cuneiform, intermediate cuneiform, and first and second metatarsals, respectively, according to one embodiment.
Figure 6A:
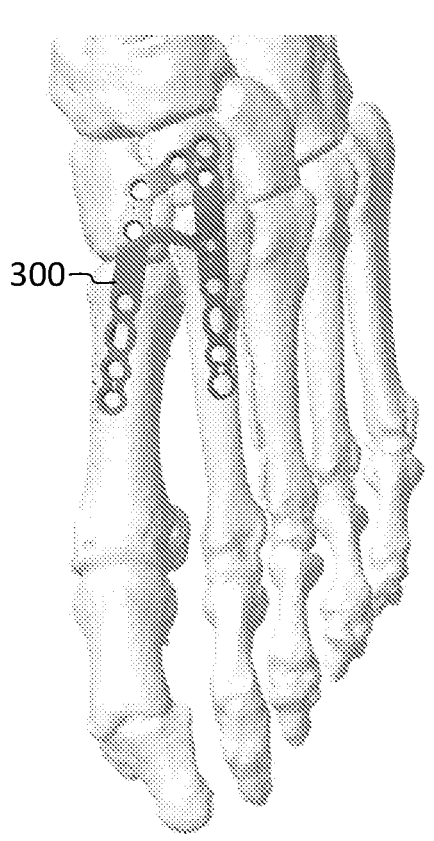
Figure 6B:
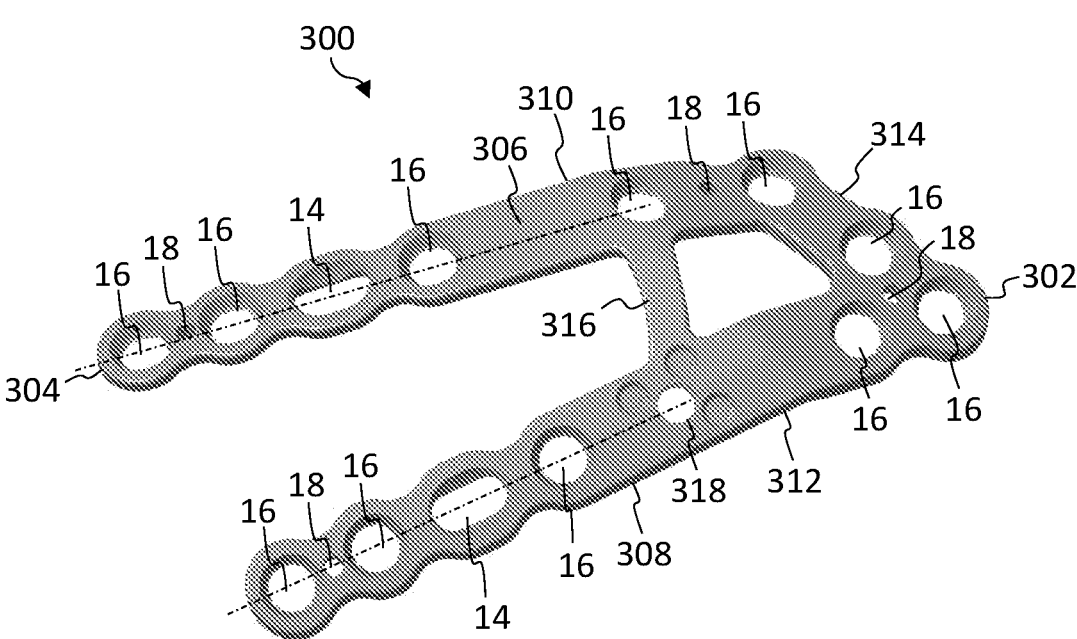

Turning now to FIGS. 6A-6E, a coupled Lisfranc $1^{st}$ & $2^{nd}$ tarsometatarsal plate 300 is shown according to one embodiment. FIG. 6A depicts the anatomy of the foot 4 with the coupled Lisfranc $1^{st}$ & $2^{nd}$ tarsometatarsal plates 300 contoured to sit on the dorsal aspect of the medial cuneiform, intermediate cuneiform, $1^{st}$ metatarsal and $2^{nd}$ metatarsal, respectively. The coupled plate 300 has a bifurcated body that extends from a first end or proximal end 302 configured to sit on the medial and intermediate cuneiforms to a second end or distal end 304 configured to sit on the bodies of the $1^{st}$ and $2^{nd}$ metatarsals, respectively. The plate 300 includes a top surface 306 and an opposite, bottom surface 308 configured to contact adjacent bone. As best seen in FIG. 6B, the coupled plate 300 includes first and second legs 310, 312 connected by a proximal crossbeam 314. The crossbeam 314 is a transverse beam or connector for the legs 310, 312 at the proximal end 302 of the plate 300. The plate 300 may also include a bridge 316 that links the two legs 310, 312 of the plate 300 together for added strength.

Figure 6C:
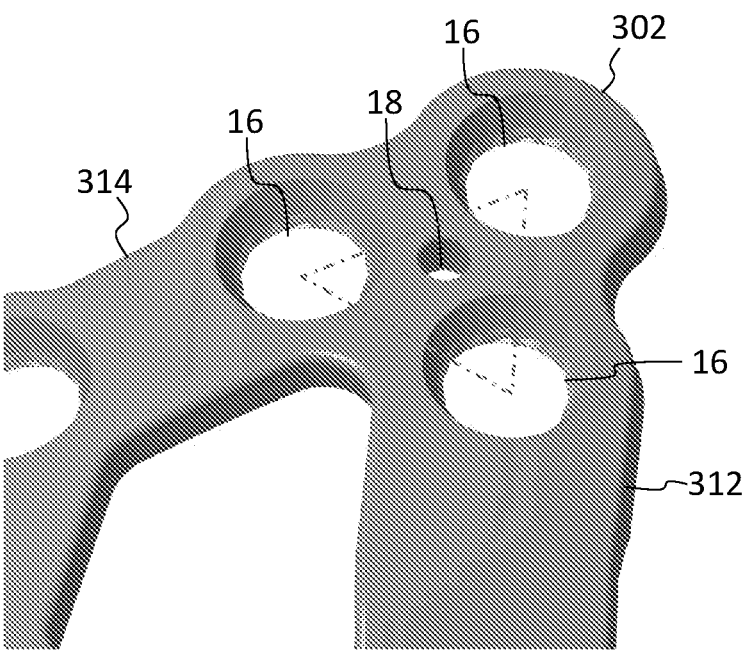
Figure 6D:
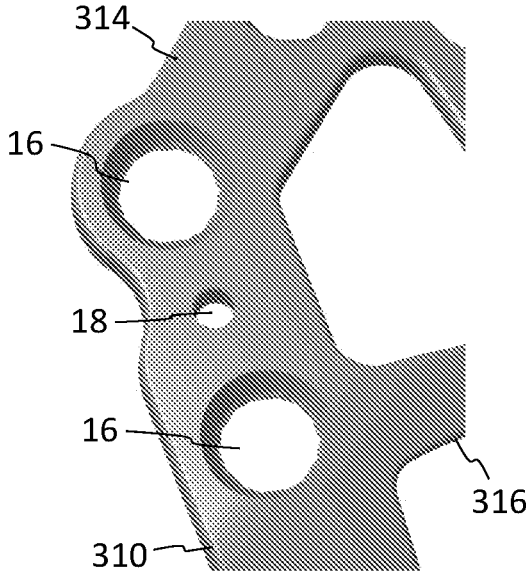

With emphasis on FIG. 6C, the proximal end 302 of the plate 300 includes a cluster of three polyaxial holes 16 configured to place one or more screws 12 into the intermediate cuneiform. The three-hole cluster may be defined at the proximal-most intersection of the leg 312 and crossbeam 314. The three-hole cluster may be aligned in a symmetrical pattern at the vertices of a triangle, such as an equilateral triangle. A K-wire hole 18 may be positioned centrally between the cluster. As shown in FIG. 6D, two additional polyaxial holes 16 may be positioned adjacent to the cluster of polyaxial holes 16, which are configured to place one or more screws 12 into the medial cuneiform. The two additional polyaxial holes 16 may be defined along the intersection of leg 310 and crossbeam 314. A K-wire hole 18 may be positioned between them. The two additional polyaxial holes 16 may be spaced or separated apart in order to make room for a Lisfranc independent screw that may be placed outside of the plate 300.

Figure 6E:
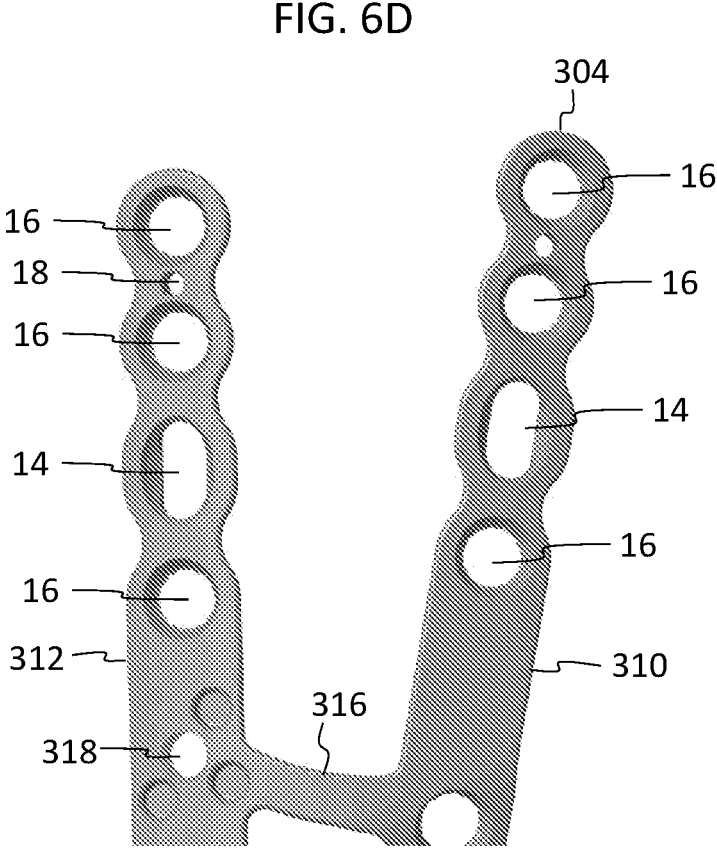

As shown in FIG. 6E, the distal end 304 of the plate 300 includes the free ends of the two legs 310, 312 that provide a series of polyaxial holes 16 to fixate the $1^{st}$ and $2^{nd}$ metatarsals. For example, three polyaxial holes 16 may be provided in each leg 310, 312 in a linear arrangement. The legs 310, 312 may be angled apart such that the free ends of the legs 310, 312 are farthest apart to mimic a normal inter-metatarsal (IM) angle between the $1^{st}$ and $2^{nd}$ metatarsals. Each leg 310, 312 may also define one dynamic compression slot 14 to assist in compression of the joints. The dynamic compression slot 14 may be positioned between the second and third polyaxial holes 16. A K-wire hole 18 may be provided between the first and second polyaxial holes 16. Some portions of the outer edges of the plate 300 may be scalloped or wavy to follow the hole pattern, minimizing potential soft tissue irritation.

The coupled plates 300 may further include a jig connection interface 318, which allows a separate jig (not shown) to connect to the plate 300 to help with placing the Lisfranc independent screw. The jig connection interface 318 may include a threaded connection with a plurality of recesses. For example, three circular recesses may be spaced around a threaded through hole. The jig connection interface 318 may be located on the top surface 306 of leg 312 adjacent to bridge 316. The coupled plates 300 may be offered in small, medium, and large sizes as well as left and right configurations.

Figure 7A:
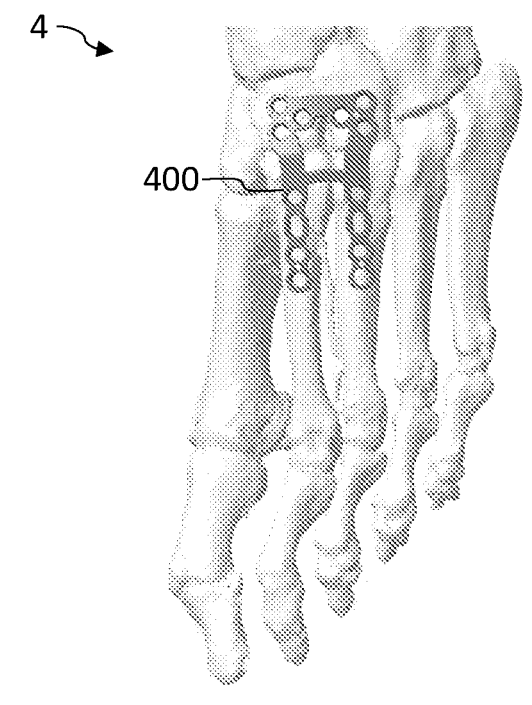
FIGS. 7A-7D depict a coupled Lisfranc second and third tarsometatarsal plate sitting on the dorsal aspect of the intermediate cuneiform, lateral cuneiform, and second and third metatarsals, respectively, according to one embodiment.
Figure 7B:
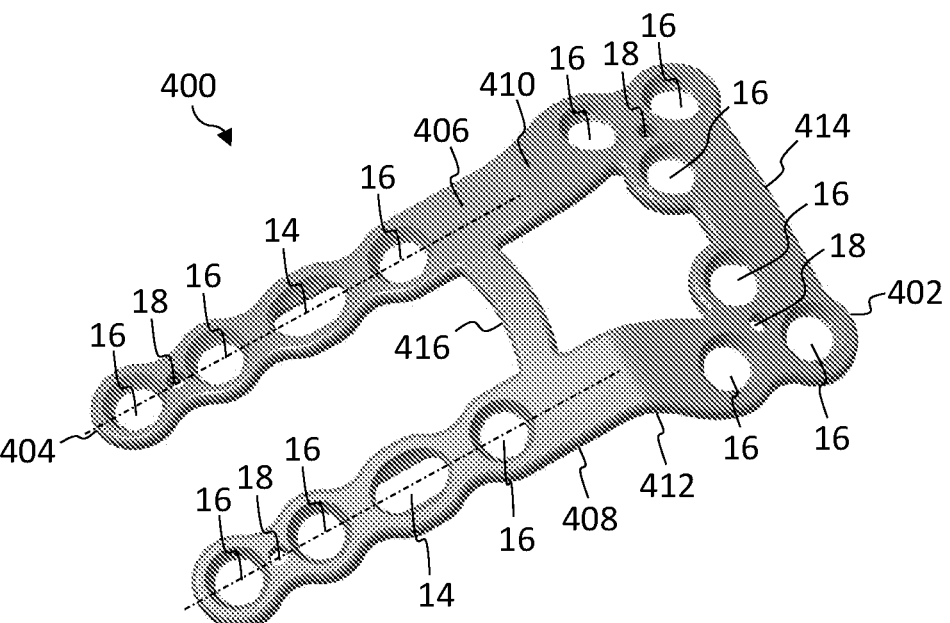

Turning now to FIGS. 7A-7D, a coupled Lisfranc $2^{nd}$ & $3^{rd}$ tarsometatarsal plate 400 is shown according to one embodiment. Coupled plate 400 is similar to plate 300 with an additional cluster of polyaxial holes 16 at the proximal end 402. As shown in FIG. 7A, the coupled Lisfranc $2^{nd}$ & $3^{rd}$ tarsometatarsal plates 400 are contoured to sit on the dorsal aspect of the intermediate cuneiform, lateral cuneiform, $2^{nd}$ metatarsal and $3^{rd}$ metatarsal, respectively. Similar to plate 300, the coupled plate 400 has a bifurcated body that extends from a first end or proximal end 402 configured to sit on the intermediate and lateral cuneiforms to a second end or distal end 404 configured to sit on the bodies of the $2^{nd}$ and $3^{rd}$ metatarsals, respectively. The plate 400 includes a top surface 406 and an opposite, bottom surface 408 configured to contact adjacent bone. As best seen in FIG. 7B, the coupled plate 400 includes first and second legs 410, 412 connected by a proximal crossbeam 414. The crossbeam 414 may be a horizontal or transverse beam for the legs 410, 412 at the proximal end 402 of the plate 400.

Figure 7C:
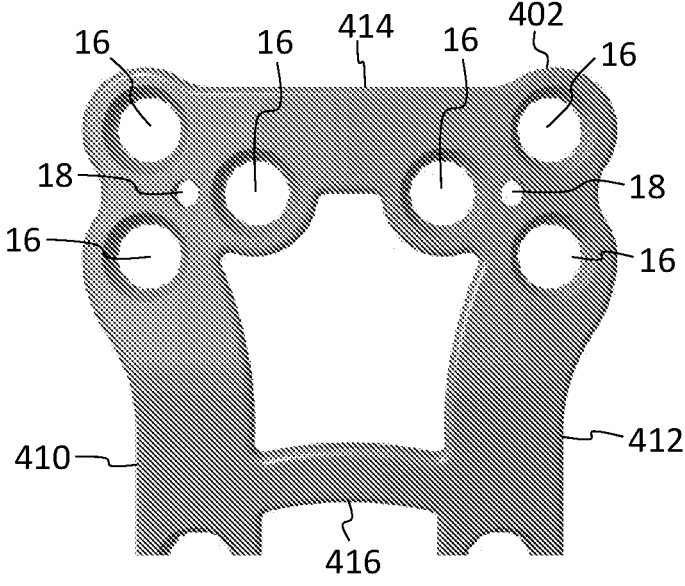
Figure 7D:
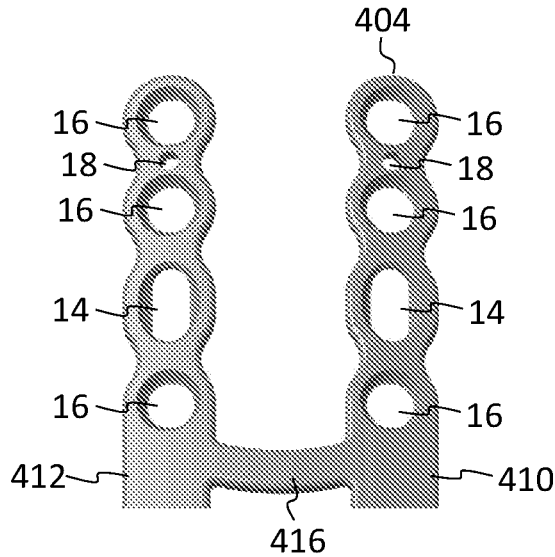

As best seen in FIG. 7C, the proximal end 402 of the plate 400 may include two symmetrical clusters of three polyaxial holes 16 designed to place one or more screws 12 into the intermediate and lateral cuneiforms, respectively. Each hole cluster may be arranged with the hole axes aligned in an equilateral triangle. The bridge 416 may include a thin curved connection linking the two legs 410, 412 of the plate 400 together for added strength to the plate 400. As shown in FIG. 7D, the distal end 404 of the plate 400 includes the free ends of the two legs 410, 412, which provides polyaxial hole options to fixate the $1^{st}$ and $2^{nd}$ metatarsals, respectively. The holes of a given leg 410, 412 may be aligned with one another in a linear fashion. The legs 410, 412 may be generally parallel to each other and may be less wide than the proximal end 402 of the plate 400. Each leg 410, 412 may define a dynamic compression slot 14 to assist in compression of the joints and/or K-wire opening 18 to temporarily secure the plate 400. The outer edges of the distal legs 410, 412 may be scalloped or wavy to follow the hole pattern, minimizing potential soft tissue irritation. These plates 400 may be offered in small, medium, and large sizes and can be used on either the left or right foot.

Figure 8A:
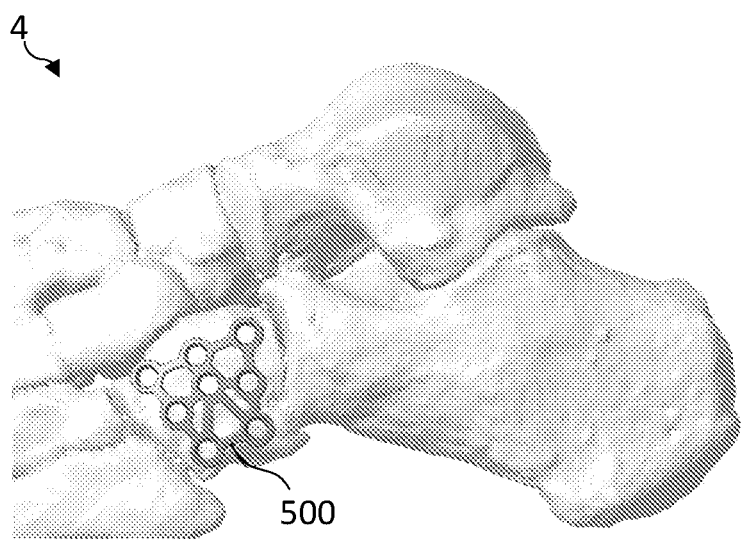
FIGS. 8A-8B depict a cuboid plate sitting on a dorsal aspect of the cuboid according to one embodiment.
Figure 8B:
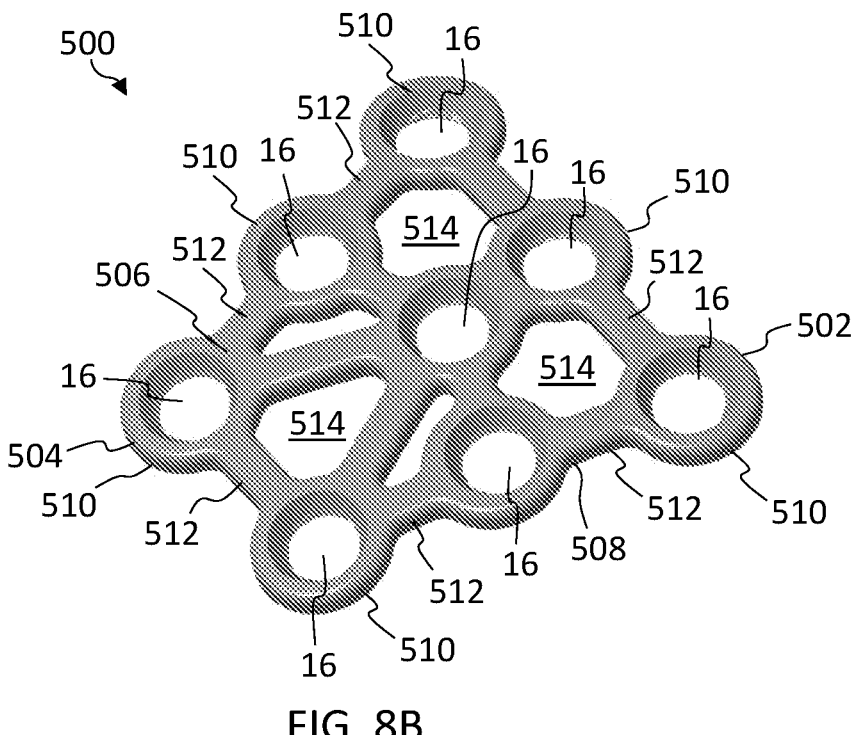

Turning now to FIGS. 8A-8B, a cuboid plate 500 is shown according to one embodiment. As shown in FIG. 8A, the cuboid plate 500 is contoured to sit laterally on the cuboid bone, which is roughly cubical in shape. Depending on its orientation, the plate 500 may extend from a first end 502, which aligns generally dorsally and superiorly, to a second end 504, which aligns generally plantar and inferiorly on the cuboid bone. The plate 500 may have an outer trapezoidal shape to match the general shape of the cuboid bone. For example, the first end 502 may have a greater width than the second end 504 and the first and second ends 502, 504 may be generally parallel with one another. The plate 500 includes a top surface 506 and an opposite, bottom surface 508 configured to contact the bone.

The cuboid plate 500 defines a plurality of polyaxial holes 16 between the top and bottom surfaces 506, 508. Each hole 16 may be enclosed by a thin ring 510. One or more rings 510 may be connected together via struts 512 forming a lattice-like structure. For example, the cuboid plate 500 may include eight polyaxial holes 16 that are linked with thin struts 512. Seven polyaxial holes 16 may be connected around the perimeter of the trapezoid and the eighth hole 16 may be interconnected near the middle of the plate 500. Larger openings or through spaces 514 may remain between the connections. The thinner configuration of the rings 510 and struts 512 along with the through spaces 514 may allow the plate 500 to be shaped or contoured. The network of rings 510 and struts 512 maintain plate strength and provide some flexibility to the plate 500. The cuboid plate 500 may be used on the left or right foot.

Figure 9A:
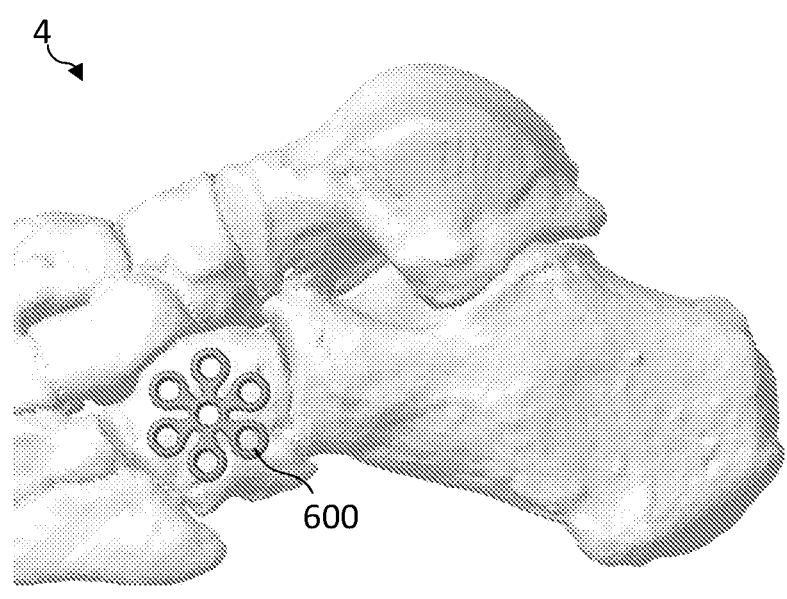
FIGS. 9A-9B depict a flower plate sitting on a dorsal aspect of the cuboid according to one embodiment.
Figure 9B:
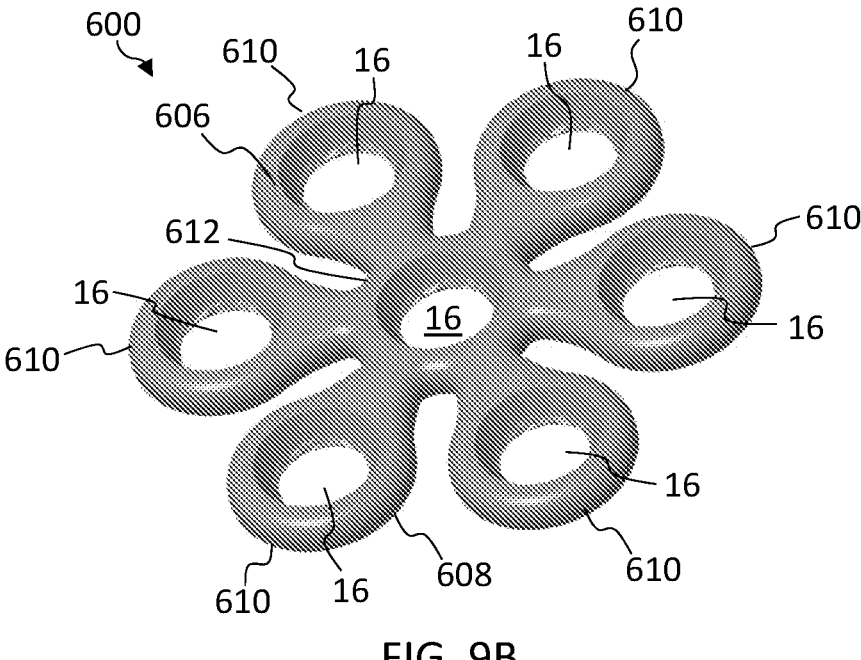

Turning now to FIGS. 9A-9B, a flower plate 600 is shown according to one embodiment. As shown in FIG. 9A, the flower plate is contoured to sit laterally on the cuboid bone. Due to its symmetrical design, the plate 600 looks the same in any direction. The plate 600 includes a top surface 606 and an opposite, bottom surface 608 configured to contact the bone. The flower plate 600 has petal-like or lobe-like extensions 610 radiating outward from a central circular region 612. Each lobe extension 610 may start with a narrower end connected to the central circular region 612 that broadens to the rounded free end. In one embodiment, the flower plate 600 has six petal-like or lobe-like extensions 610 radiating outward from the central circular region 612. The central circular region 612 encloses one central polyaxial hole 16 located at the core of the plate 600. Each of the lobes or extensions 610 also defines a polyaxial hole 16, for example, as a rim or ring encircling the hole 16. The flower shape is configured to better fit the shape of the cuboid and fixate cuboid fractures. The flower plate 600 may be used on the left or right foot.

Figure 10A:
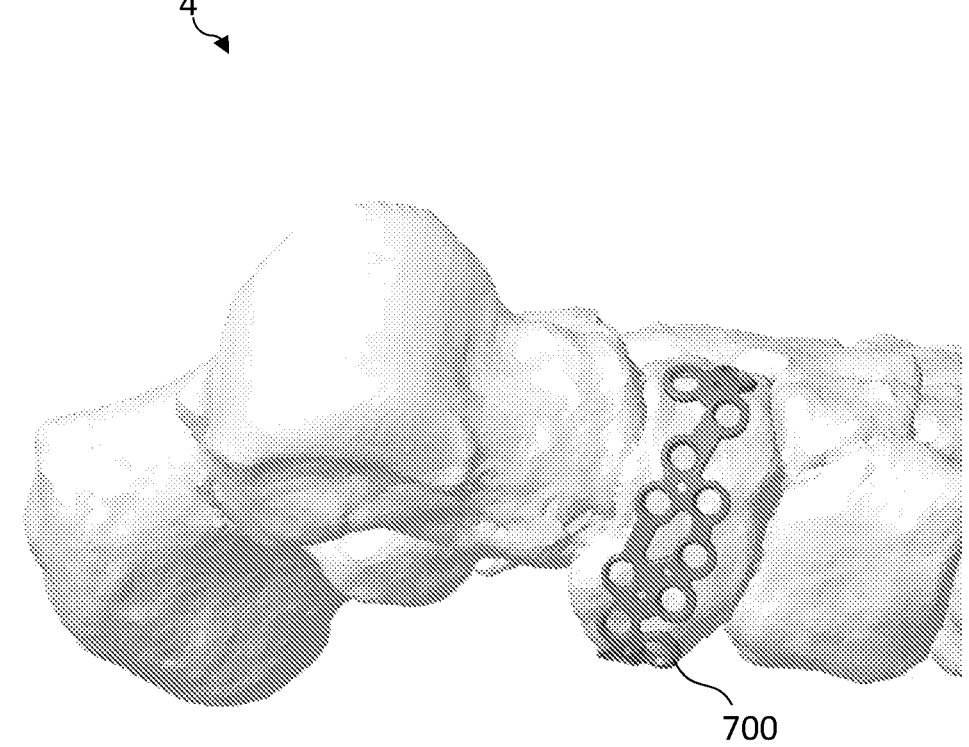
FIGS. 10A-10C depict a navicular plate with plantar bundle and optional plantar extension sitting dorsally and wrapping plantar on the navicular according to one embodiment.
Figure 10B:
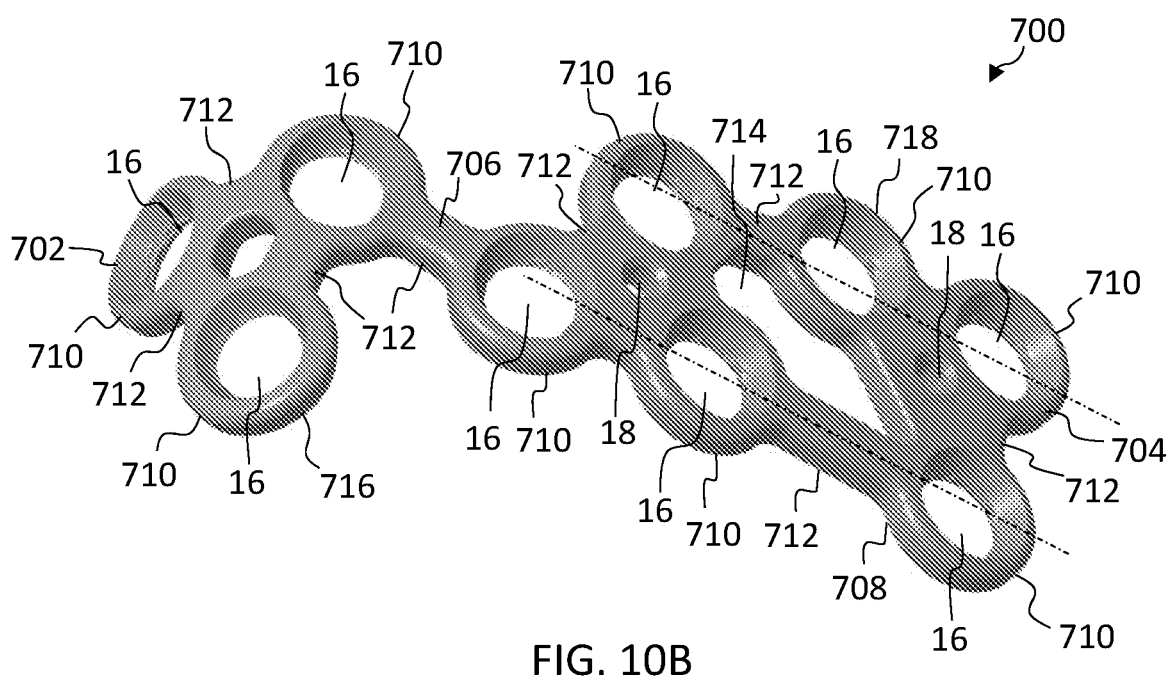

Turning now to FIGS. 10A-10E, a navicular plate 700 is shown according to one embodiment. As shown in FIG. 10A, the navicular plate 700 is contoured to sit dorsally on the navicular bone. The navicular bone is one of seven bones that make up the tarsus of the ankle and foot. The navicular bone is located on the top medial side of the middle foot, next to the cuboid bone, anterior to the head of the talus and posterior to the cuneiform bones. As shown in FIG. 10B, the navicular plate 700 has a body that extends from a first end or superior dorsal end 702 configured to sit on the top of the navicular bone to a second end or inferior medial end 704 configured to sit toward the medial side and/or bottom of the navicular bone. The plate 700 includes a top surface 706 and an opposite, bottom surface 708 configured to contact adjacent bone. The navicular plate 700 defines a plurality of polyaxial holes 16 between the top and bottom surfaces 706, 708. Each hole 16 may be enclosed by a thin ring 710. One or more rings 710 may be connected together via struts 712. One or more larger openings or through spaces 714 may remain between some connections. The plate 700 may be divided into a dorsal lateral section 716, a main section 718, and an optional plantar bundle extension 720.

Figure 10C:
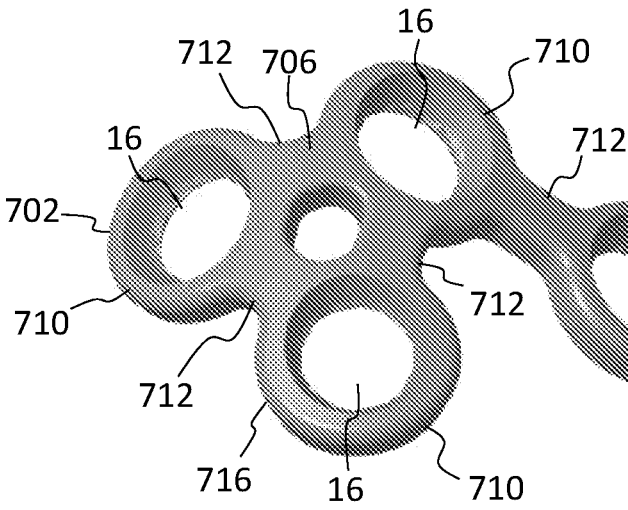

As shown in FIG. 10C, the dorsal lateral section 716 of the plate 700 may include a three-hole cluster that wraps laterally onto the unique shape of the navicular. The cluster of three polyaxial holes 16 is configured to place one or more screws 12 into the superior dorsal aspect of the navicular bone. The three-hole cluster may be in a symmetrical pattern at the vertices of a triangle with struts 712 connecting each ring 710 into the triangular shape. The triangle may be an equilateral triangle and the rings 710 may be curved or contoured such that the axis of each hole 16 points centrally together into the bone. The dorsal lateral section 716 may be bent or contoured to mimic the convex dorsal surface of the navicular. The dorsal lateral section 716 may be attached to the main section 718 with one strut 706.

The main section 718 of the plate 700 may include two rows of polyaxial holes 16 to fixate navicular fractures. The main section 718 may include a second central three-hole cluster connected to the dorsal lateral section 716 by single strut 706. Similar to the dorsal lateral section 716, the three-hole cluster may be in a symmetrical pattern at the vertices of a triangle with struts 712 connecting each ring 710 into the triangular shape. A K-wire hole 18 may be positioned centrally between the cluster of polyaxial holes 16. A pair of struts 712 of unequal lengths and defining an open space 714 therebetween separate the second central three-hole cluster from a third hole cluster. The open space 714 may have an irregular shape defined by the outside of rings 710 and struts 712. For navicular plate 700, the third cluster forms the inferior medial end 704 of the plate 700. The third cluster may have an asymmetric pattern of polyaxial holes 16 with struts 712 connecting each ring 710 together and one or more K-wire holes 18 positioned within the cluster. For example, as best seen in FIG. 10B, the third cluster may include an asymmetric triangle of three polyaxial holes 16 with a single K-wire hole 18. When aligned with the second three-hole cluster, two rows of polyaxial holes 16 are available to accept one or more screws 12 into the medial aspect of the navicular bone. The main section 718 may be bent or contoured to mimic the convex medial surface of the navicular including the navicular tuberosity. The outer edges of the plate 700 may be scalloped or wavy to follow the hole pattern, minimizing potential soft tissue irritation.

Figure 10D:
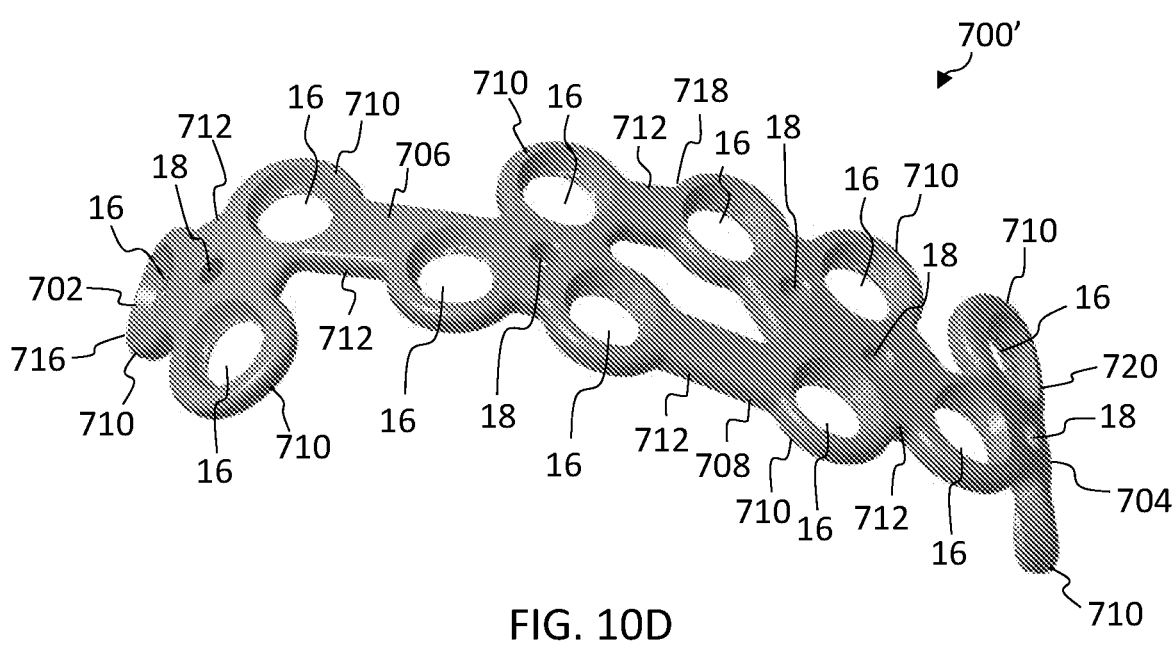
FIG. 10D shows a navicular plate with the plantar bundle extension according to one embodiment.
Figure 10E:
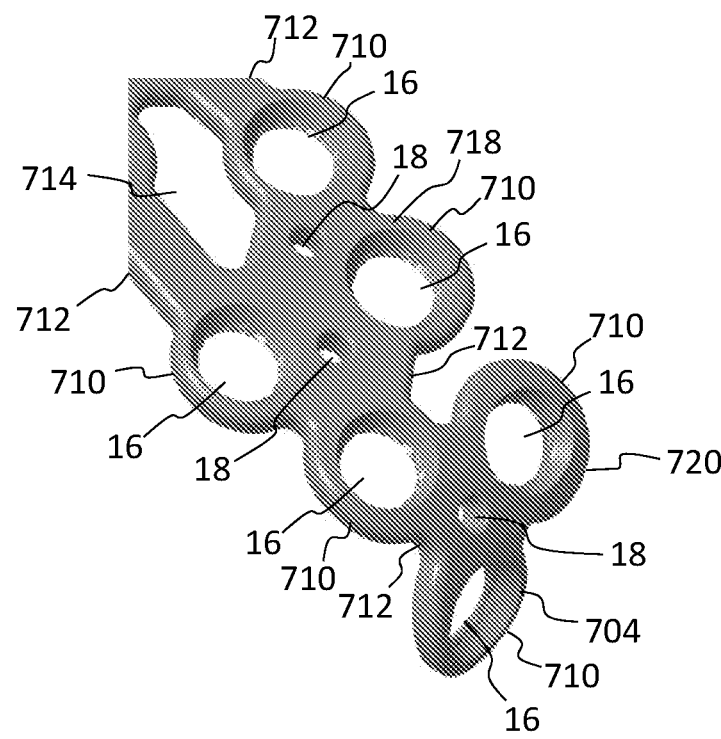
FIG. 10E shows the plantar extension with a fourth cluster of three polyaxial holes.

FIG. 10D shows a navicular plate 700' with the plantar bundle extension 720 according to one embodiment. The navicular plate 700' with plantar bundle extension 720 is identical to the navicular plate 700 but includes the plantar extension 720 that wraps plantar and medial on the navicular bone. For navicular plate 700', the plantar extension 720 forms the inferior plantar end 704 of the plate 700. As best seen in FIG. 10E, the plantar extension 720 includes a fourth cluster of three polyaxial holes 16 configured to place one or more screws 12 into the inferior medial aspect of the navicular bone. The plantar extension 720, similar to the dorsal lateral section 716, includes a three-hole polyaxial cluster having a symmetrical pattern at the vertices of a triangle with struts 712 connecting each ring 710 into the triangular shape with a central K-wire hole 18. The cluster may be arranged as an equilateral triangle but the rings 710 may be curved or contoured such that the axis of each hole 16 points in different directions into the bone. The plantar extension 720 connects to the main section 718 and adds an additional K-wire hole 18 to the main section 718. The plantar bundle extension 720 may be bent or contoured to mimic the convex plantar surface of the navicular. Navicular plates 700, 700' may be offered in left and right configurations.

Figure 11A:
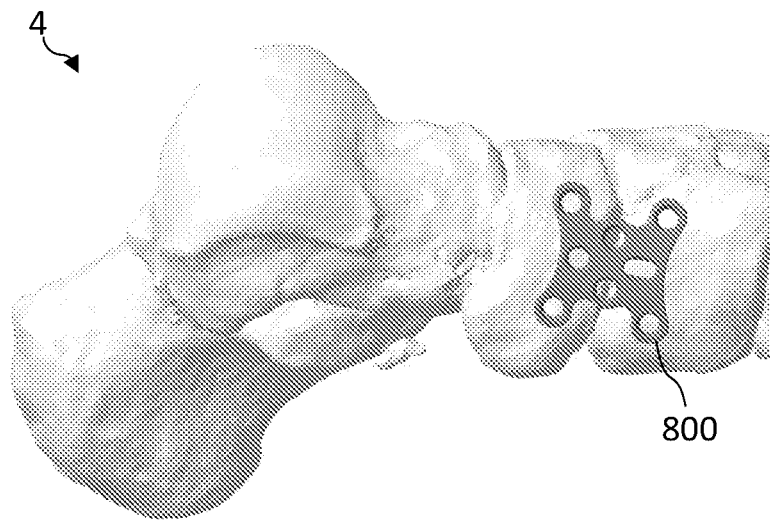
FIGS. 11A-11B depict a utility plate sitting medially over a naviculo-cuneiform joint according to one embodiment.
Figure 11B:
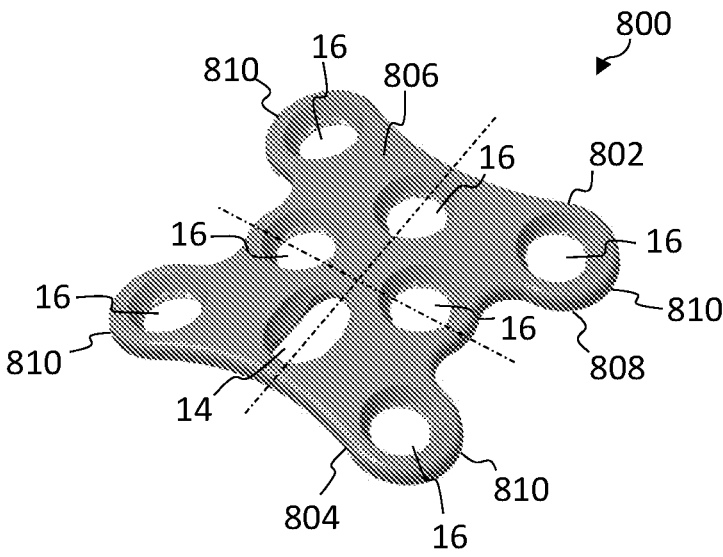

Turning now to FIGS. 11A-11B, a utility plate 800 is shown according to one embodiment. The utility plates 800 are configured to fit on multiple bones and/or span joints in the forefoot, midfoot, and hindfoot. For example, utility plate 800 may be used to fix and/or fuse together the naviculo-cuneiform (NC) joint, the talo-navicular (TN) joint, the calcaneocuboid (CC) joint, or the tarso-metatarsal (TMT) joint. FIG. 11A depicts utility plate 800 sitting medially over the naviculo-cuneiform joint. Other fractures of bones of the foot or other locations could also be fixed using utility plate 800.

As shown in FIG. 11B, the utility plate 800 may have an H-shaped body that extends from a first end 802 configured to sit on one bone (e.g., the navicular bone) to a second end 804 configured to sit on another bone (e.g., the cuneiform bone). The plate 800 includes a top surface 806 and an opposite, bottom surface 808 configured to contact adjacent bone. The H shape may be formed by four lobes or tabs 810 defining the four corners of the H shape. In this case, the plate 800 may be oriented such that tabs 810 generally point superior/inferior or dorsal/plantar on the bones. The ends 802, 804 may have a concave or inward curvature between the tabs 810.

The utility plate 800 defines a plurality of polyaxial holes 16 between the top and bottom surfaces 806, 808 for receiving one or more screws 12 to secure the plate 800 to bone. For example, one polyaxial hole 16 may be positioned in each lobe or tab 810, which straddles the joint. The plate 800 may include a polyaxial hole 16 and a dynamic compression slot 14 aligned along a central axis between the first and second ends 802, 804. The dynamic compression slot 14 is incorporated into the plate 800 where compression through the plate 800 may be beneficial. For example, the polyaxial hole 16 may receive one screw 12 into one bone (e.g., the navicular bone) and the dynamic compression slot 14 may receive another screw 12 into the adjacent bone (e.g., the cuneiform bone). This allows compression of the bone fragment(s) and/or the joint, for example, to reduce joint space, enhance stability, and promote union of the joint surfaces. A second pair of central polyaxial holes 16 may be aligned along a transverse axis, which is horizontal to the central axis. These central holes 16 may generally align with the joint between bones. It will be appreciated, however, that the utility plate 800 may be oriented in any suitable manner to secure the joint and/or bone(s). The utility plate 800 may be offered in small, medium, and large configurations, which may be used on the left or right foot.

Figure 12A:
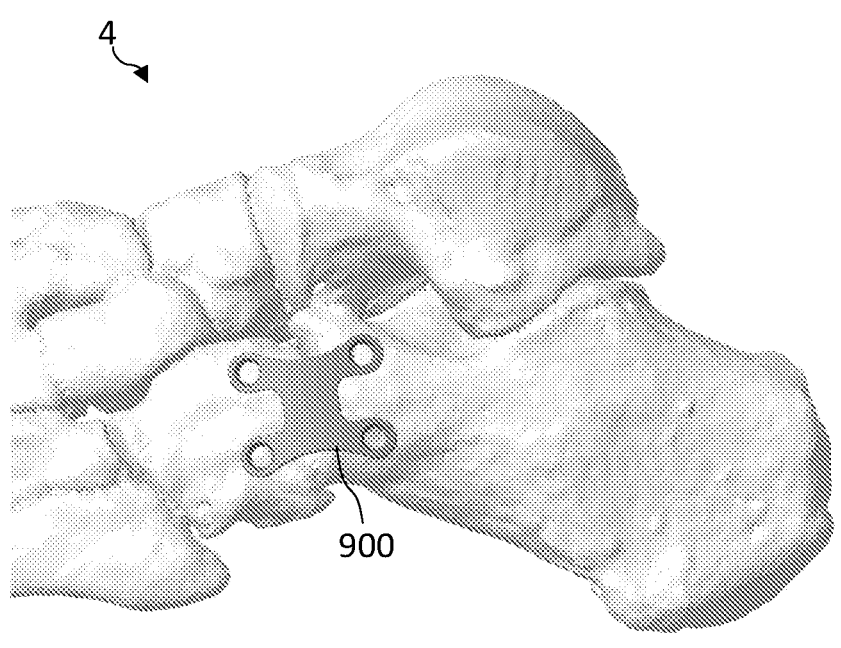
FIGS. 12A-12B depict an H-plate sitting laterally over a calcaneocuboid joint according to one embodiment.
Figure 12B:
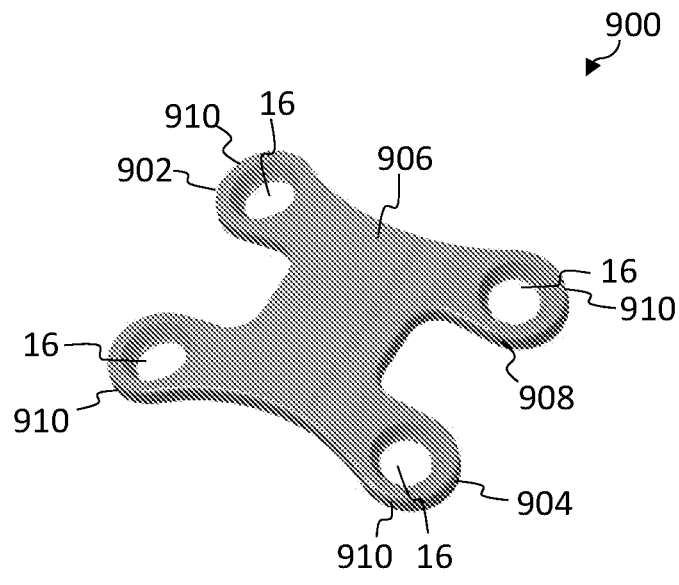

Turning now to FIGS. 12A-12B, a H-plate 900 is shown according to one embodiment. Like the utility plates 800, the H-plate 900 may have an H-shaped body configured to span a joint in the forefoot, midfoot, or hindfoot. The H-plates 900 are configured to fit across multiple joints in the forefoot, midfoot, and hindfoot. For example, the H-plates 900 may be used to fix or fuse the naviculo-cuneiform (NC) joint, the talo-navicular (TN) joint, the calcaneocuboid (CC) joint, or the tarso-metatarsal (TMT) joint, or other joints or bone fractures. FIG. 12A depicts H-plate 900 sitting laterally over the calcaneocuboid (CC) joint.

As shown in FIG. 12B, the H-plate 900 may have a solid H-shaped body that extends from a first end 902 configured to sit on one bone (e.g., the calcaneus bone) to a second end 904 configured to sit on another bone (e.g., the cuboid bone). The plate 900 includes a top surface 906 and an opposite, bottom surface 908 configured to contact adjacent bone. The H shape may be formed by four lobes or tabs 910 defining the four corners of the H shape. In this case, the plate 900 may be rotated and oriented such that tabs 910 generally point proximally/distally and extend away from the joint. Each tab 910 may define a single polyaxial hole 16. The plate 900 may be shaped like an H to provide two screw holes 16 per bone over the joint line. The screw holes 16 may be located on tabs 910 to allow for easier bending. This gives the surgeon the ability to bend screw holes down to bone that may be sitting off plane in relation to the adjacent bone across a joint line. This plate style may be offered in small, medium, and large configurations for the left and right foot.

Figure 13A:
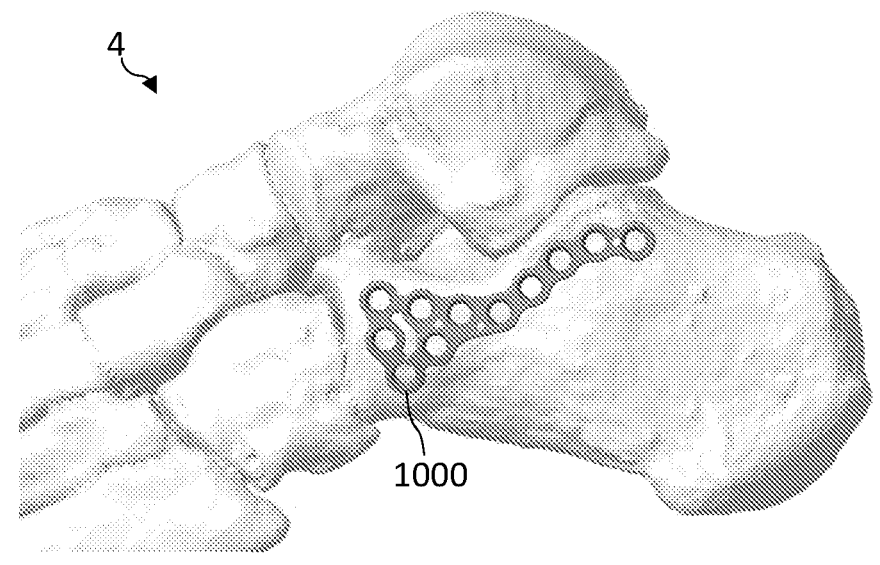
FIGS. 13A-13C depict a sinus tarsi wave plate sitting laterally on the calcaneus and rafting subtalar joint according to one embodiment.
Figure 13B:
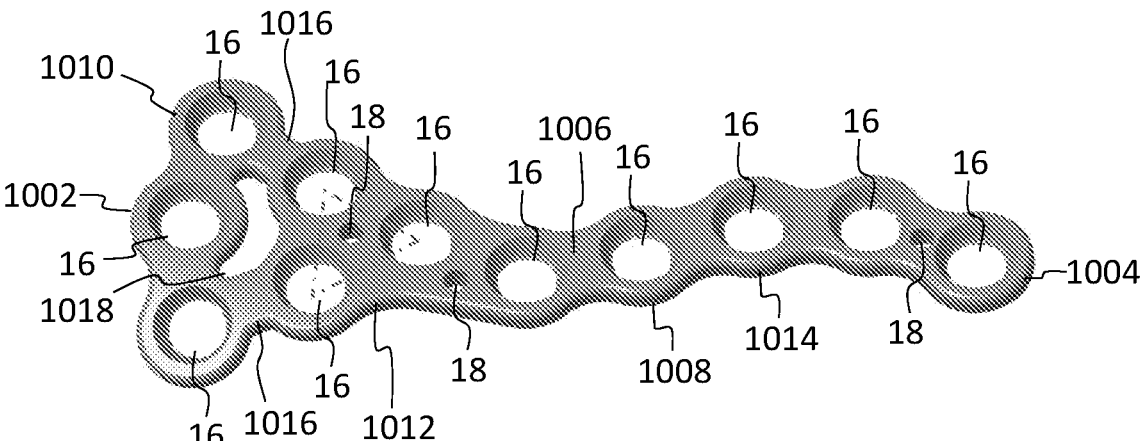
Figure 13C:
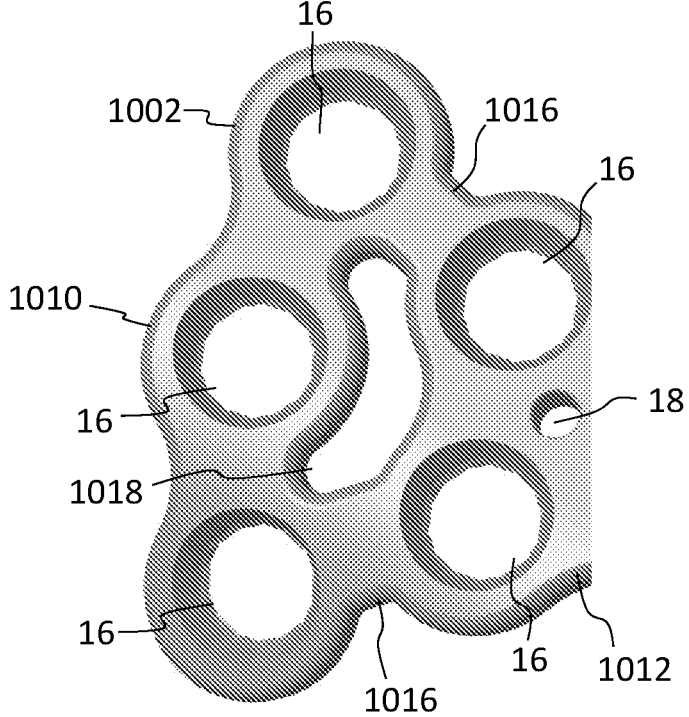

Turning now to FIGS. 13A-13C, a sinus tarsi wave plate 1000 is shown according to one embodiment. The sinus tarsi wave plates 1000 are contoured to sit laterally on the calcaneus below the talus. The sinus tarsi approach is used for minimally invasive reductions and percutaneous fixation of displaced intraarticular calcaneal fractures. As shown in FIG. 13A, the sinus tarsi wave plate 1000 sits on the lateral aspect of the calcaneus just plantar to the subtalar joint and follows the natural wave shape made by this joint line. The plate contour may match the critical angle of Gissane (e.g., between about 130-145 degrees) to provide screw hole locations to raft the subtalar joint surface to prevent collapse.

As shown in FIG. 13B, the sinus tarsi wave plate 1000 may have an elongated body that extends from a first anterior end 1002 configured to sit on the anterior aspect of the calcaneus to a second posterior end 1004 configured to sit on the lateral aspect of the calcaneus below the subtalar joint. The plate 1000 includes a top surface 1006 and an opposite, bottom surface 1008 configured to contact adjacent bone. The sinus tarsi wave plate 1000 may be divided into an anterior section 1010, a main body 1012, and a posterior section 1014.

With further emphasis on FIG. 13C, the anterior portion 1010 of the plate 1000 provides screw holes 16 for any fracture of the anterior aspect of the calcaneus. The three most anterior screw holes 16 may be offset from the main body 1012 of the plate 1000 with two tabs 1016 connecting them. The anterior portion 1010 may be separated from the main body 1012 by an irregular interspace 1018. The tabs 1016 may be angled toward one another as they connect to the main body 1012. These tabs 1016 can be cut easily in the case where the anterior portion of the calcaneus is intact.

The main body 1012 may include a three-hole polyaxial cluster, for example, having a symmetrical pattern. The axis of each hole 16 in the three-hole cluster may be located at the vertices of an equilateral triangle. A central K-wire hole 18 may be located within the cluster. The posterior section 1014 may include a tail extending posteriorly from the main body 1012. The posterior section 1014 may include a plurality of polyaxial holes 16 following the wave of the subtalar joint. For example, five holes 16 may be provided in series mimicking the curvature of a wave or undulation. The trough of the wave may begin at the main body 1012 and the crest of the wave may peak toward the posterior end 1004. The outer edges of the plate 1000 may be scalloped or wavy to follow the hole pattern, minimizing potential soft tissue irritation. Additional K-wire holes 18 may be placed, for example, between the posterior-most hole 16 and the adjacent hole 16 and between the three-hole cluster and the next adjacent hole 16 along the posterior section 1014. The sinus tarsi wave plates 1000 may be offered in small and large sizes with left and right configurations.

Turning now to FIGS. 14A-14D, a sinus tarsi tongue plate 1000' is shown according to one embodiment. The sinus tarsi tongue plates 1000' are the same as the sinus tarsi wave plates 1000 with the addition of a posterior extension 1020 and a plantar offset extension 1022. The sinus tarsi tongue plates 1000' are contoured to sit laterally on the calcaneus below the talus and the subtalar joint. Like the sinus tarsi wave plates 1000, the sinus tarsi tongue plates 1000' sit plantar to and raft the subtalar joint.

Figure 14A:
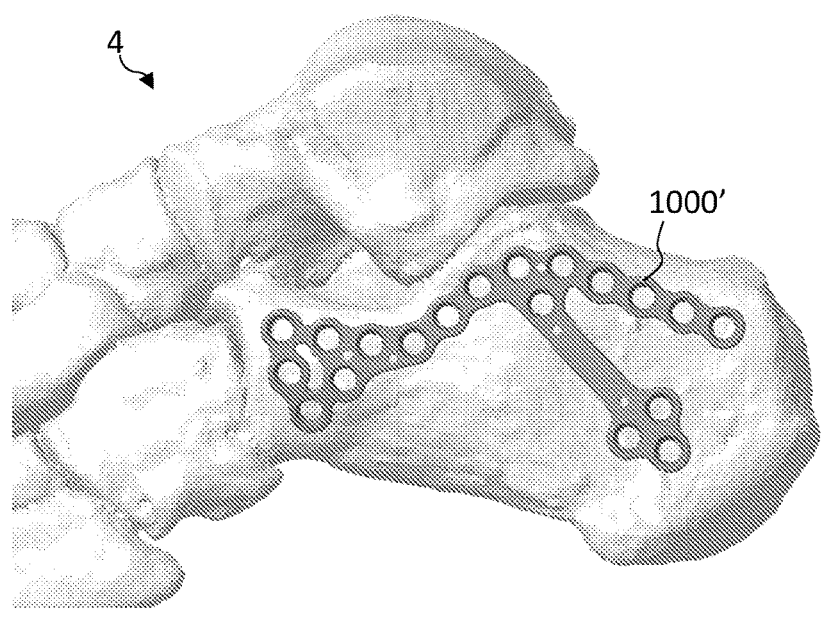
FIGS. 14A-14D depict a sinus tarsi tongue type plate sitting laterally on the calcaneus according to one embodiment.
Figure 14B:
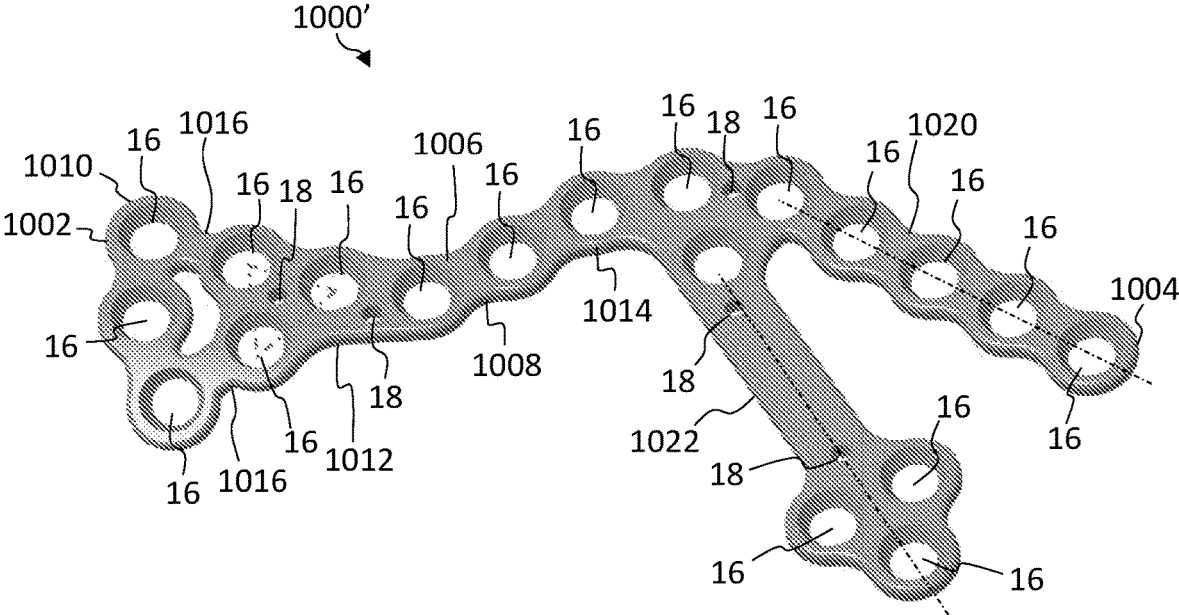
Figure 14C:
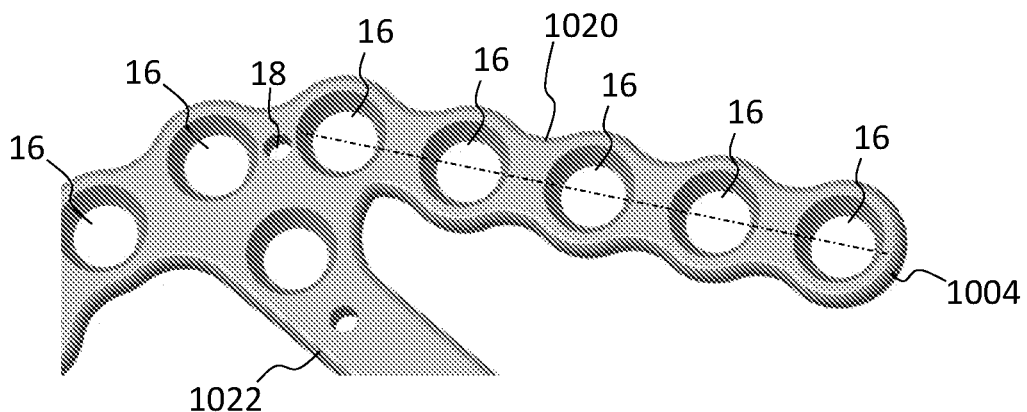

The sinus tarsi tongue plates 1000' include anterior section 1010, main body 1012, and posterior section 1014. The anterior section 1010 includes the same three-hole anterior portion 1010 that can be easily cut and removed. The main body 1012 includes the three-hole cluster and the posterior section 1014 includes the wave following the contour of the subtalar joint. As best seen in FIG. 14C, the posterior extension 1020 extends posteriorly from the free end of the posterior section 1014. The posterior extension 1020 may include a first straight continuation of the posterior section 1014. The posterior extension 1020 may include a series of polyaxial holes 16, for example, aligned in a linear arrangement. The outer edges of the posterior extension 1020 may be scalloped or wavy to follow the hole pattern. The polyaxial holes 16 in the posterior extension 1020 may act as rafting screw holes, which extend posteriorly to capture fragments of bone that may have displaced during a tongue type fracture of the calcaneus.

Figure 14D:
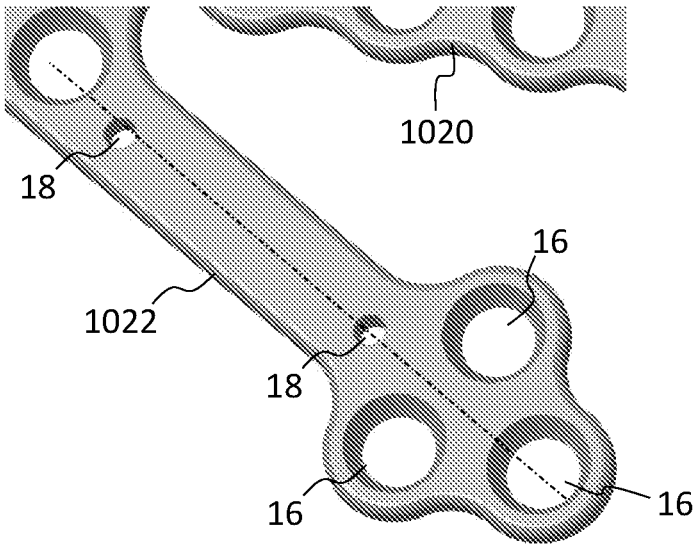

With further emphasis on FIG. 14D, the plantar offset extension 1022 may extend posteriorly and plantar from the free end of the posterior section 1014. The plantar offset extension 1022 may include a second straight continuation of the posterior section 1014 angled relative to the posterior extension 1020. The plantar offset extension 1022 may have a solid linear body that terminates with a three-hole cluster. The three-hole cluster may define holes 16 with axes in a symmetrical pattern at the vertices of a triangle. The addition of extensions 1020, 1022 may create another three-hole cluster at the intersection of the posterior section 1014 and extensions 1020, 1022. One or more K-wire holes 18 may be positioned along the length of the extensions 1020, 1022. The posterior plantar offset 1022 defines screw holes 16 that may receive screws 12 configured to capture fragments of bone that may be displaced plantar in the calcaneus. Either or both of the plate extensions 1020, 1022 may be cut off by the surgeon if they are not needed. The sinus tarsi tongue plate 1000' may be offered in small and large sizes with left and right configurations.

Figure 15A:
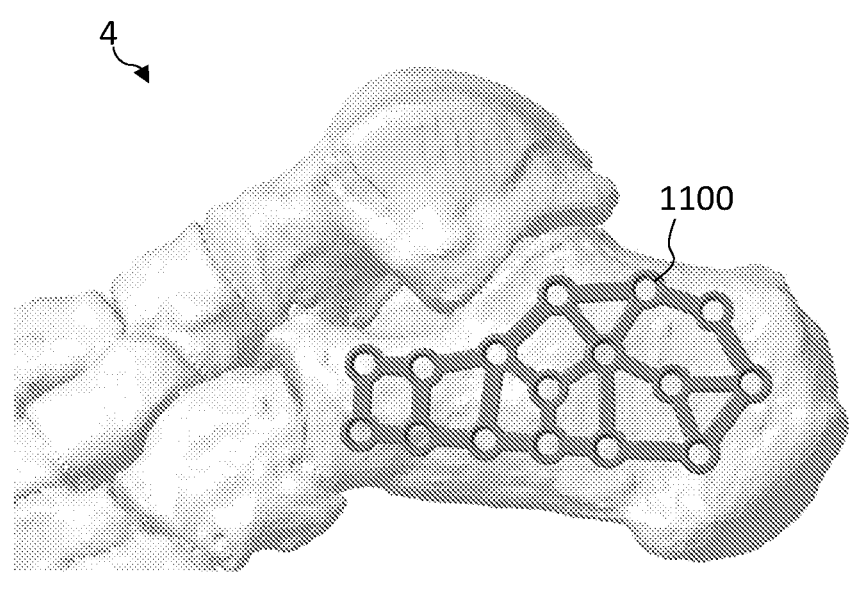
FIGS. 15A-15B depict a calcaneus perimeter plate sitting laterally on the calcaneus with perimeter and mesh screw holes according to one embodiment.
Figure 15B:
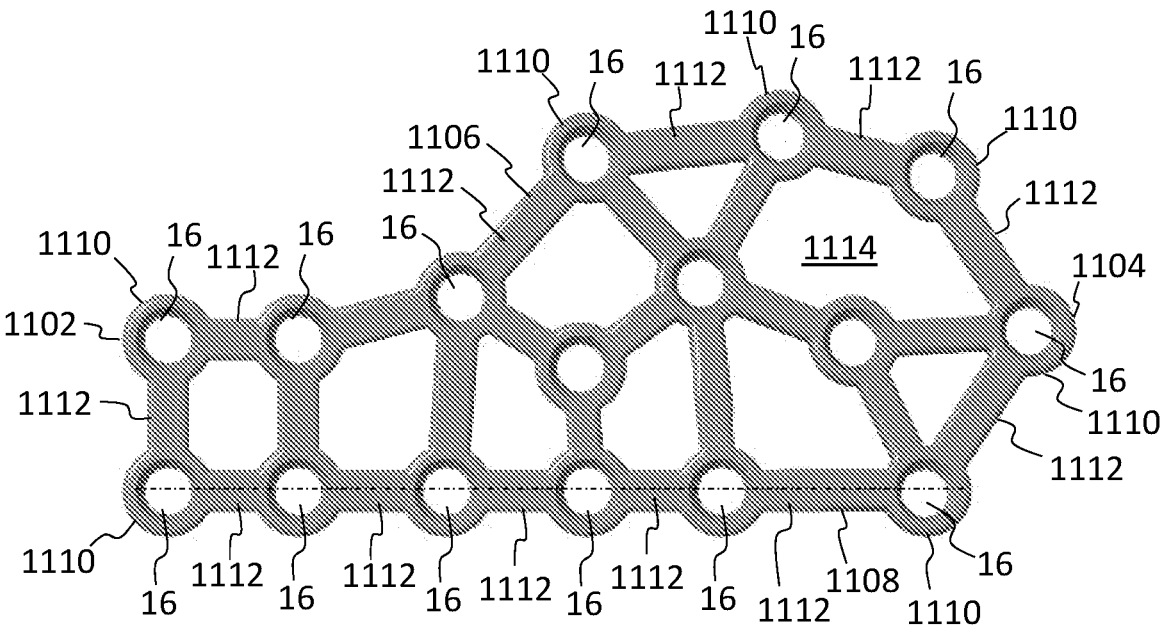

Turning now to FIGS. 15A-15B, a calcaneus perimeter plate 1100 is shown according to one embodiment. As shown in FIG. 15A, the calcaneus perimeter plates 1100 are contoured to sit laterally on the calcaneus. The calcaneus perimeter plate 1100 may be utilized for severe fractures of the calcaneus where there are multiple fractures and displaced fragments. The calcaneus perimeter plate 1100 is configured to line the perimeter of the calcaneus in order to get screws in the cortical bone for structural stability and piece the calcaneus back together as close to its original shape as possible. The calcaneus perimeter plate 1100 may act as a backboard to hold the fragments of the calcaneus until the bone starts to heal.

The calcaneus perimeter plate 1100 extends from a first anterior end 1002 configured to sit laterally on the anterior aspect of the calcaneus to a second posterior end 1004 configured to sit laterally on the posterior aspect of the calcaneus. The plate 1100 includes a top surface 1106 and an opposite, bottom surface 1108 configured to contact the bone. The calcaneus perimeter plate 1100 defines a plurality of polyaxial holes 16 between the top and bottom surfaces 1106, 1108. Each polyaxial hole 16 may be enclosed by a ring 1110. One or more rings 1110 may be connected together via struts 1112 forming a lattice structure. Larger openings or through spaces 1114 may remain between the connections. In one embodiment, a perimeter of thirteen perimeter rings 1110 may be linked together with perimeter struts 1112. The perimeter may mimic the lateral side of the calcaneus, for example, having a smaller quadrilateral shape on the anterior end 1102 and a larger rounded shape on the posterior end 1104. In an exemplary embodiment, the perimeter rings 1110 align with the perimeter of the calcaneus such that screws 12 may be inserted directly into the cortical bone of the calcaneus, ensuring structural stability.

Additional screw holes 16 and inner struts 112 may be located on the inside of the perimeter of the plate 1100. In one embodiment, three inner rings 1110 may be linked together and with the surrounding perimeter rings 1110. The inner rings 1110 and inner struts 112 may provide cross-bracing to maintain plate strength and provide some flexibility to the plate 1100. The inner holes 16 provide additional points of fixation of the displaced fragments and a surface for the bone to pull against. The calcaneus perimeter plates 1100 may be offered in small, medium, and large sizes as well as left and right configurations.

Figure 16A:
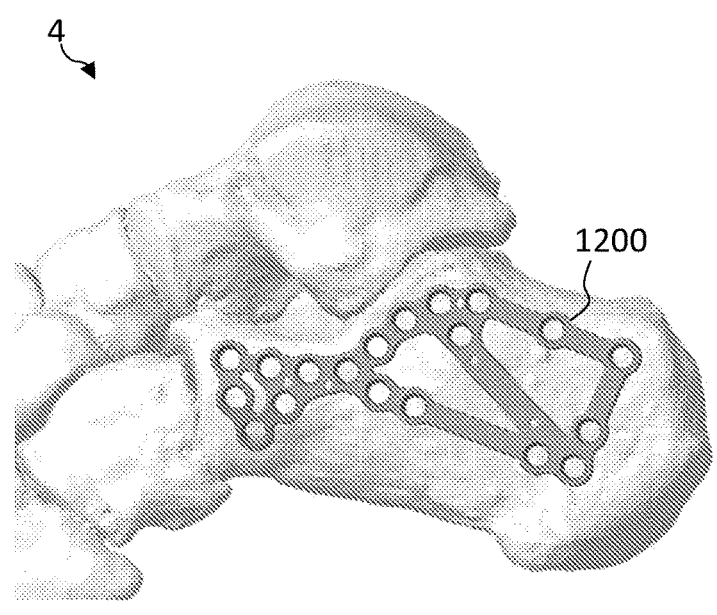
FIGS. 16A-16B depict a rafting perimeter plate sitting laterally on the calcaneus with rafting and perimeter screw hole locations according to one embodiment.
Figure 16B:
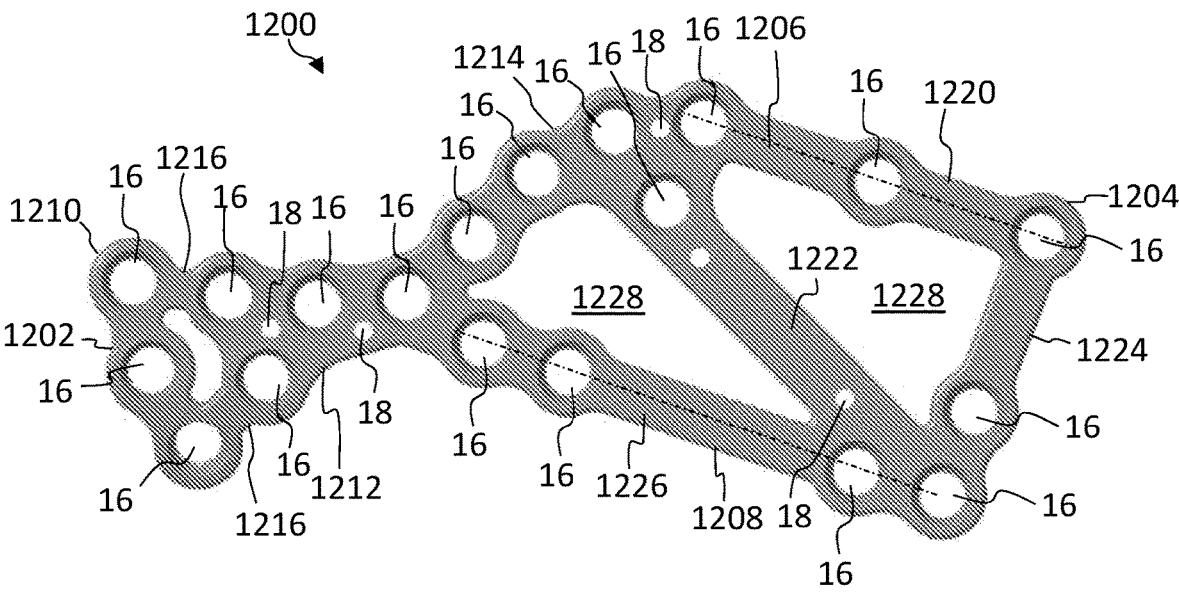

Turning now to FIGS. 16A-16B, a rafting perimeter plate 1200 is shown according to one embodiment. The rafting perimeter plates 1200 provide a hybrid approach of rafting the subtalar joint like the sinus tarsi wave plates 1000 and providing perimeter fixation to the calcaneus like the calcaneus perimeter plates 1100. This gives a surgeon the option to fixate a severe calcaneus fracture along the perimeter while providing rafting screw options and support for the subtalar joint. The rafting perimeter plates 1200 also feature struts to help contain the fragments that displaced during the fracture. As shown in FIG. 16A, the rafting perimeter plate 1200 sits laterally on the calcaneus with rafting and perimeter screw hole locations.

Turning now to FIG. 16B, the rafting perimeter plate 1200 extends from a first anterior end 1202 configured to sit laterally on the anterior aspect of the calcaneus to a second posterior end 1204 configured to sit laterally on the posterior aspect of the calcaneus below the subtalar joint. The plate 1200 includes a top surface 1206 and an opposite, bottom surface 1208 configured to contact adjacent bone. The parts of the rafting perimeter plate 1200 may include an anterior section 1210, a main body 1212, and a posterior section 1214, a posterior extension 1220, a plantar offset extension 1222, a cross member 1224, and a rear connecting extension 1226.

Similar to the sinus tarsi wave plate 1000, the anterior section 1210 of the plate 1200 may include three anterior screw holes 16 offset from the main body 1212 of the plate 1200. A pair of angled tabs 1216 may connect the three anterior screw holes 16 to the main body 1212, which can be easily cut if that portion of the plate 1200 is not needed because the anterior portion of the calcaneus is intact. The main body 1212 of plate 1200 may include a three-hole polyaxial cluster, for example, having a symmetrical pattern with a central K-wire hole 18. The axis of each hole 16 in the three-hole cluster may be located at the vertices of an equilateral triangle. The posterior section 1214 may include a wavy tail extending posteriorly from the main body 1212.

The posterior section 1214 may define a plurality of polyaxial holes 16 following the wave of the subtalar joint.

Similar to the sinus tarsi tongue plates 1000', plate 1200 includes posterior extension 1220 and plantar offset extension 1222. The posterior extension 1220 extends posteriorly from the free end of the posterior section 1214. The posterior extension 1220 may include a first straight continuation of the posterior section 1214. The posterior extension 1220 may include a series of polyaxial holes 16, for example, aligned in a linear arrangement. The polyaxial holes 16 in the posterior extension 1220 may act as rafting screw holes, which extend posteriorly to capture fragments of bone that may have displaced during a tongue type fracture of the calcaneus.

The plantar offset extension 1222 may extend posteriorly and plantar from the free end of the posterior section 1214. The plantar offset extension 1222 may include a second straight continuation of the posterior section 1214 angled relative to the posterior extension 1220. The plantar offset extension 1222 may have a solid linear body that terminates with polyaxial holes 16. The posterior plantar offset 1222 defines screw holes 16 that may receive screws 12 configured to capture fragments of bone that may be displaced plantar in the calcaneus.

The plantar offset extension 1222 is connected to the posterior extension 1220 by cross member 1224. The cross member 1224 may be a straight beam connecting the free end of the planar offset extension 1222 to the free end of the posterior extension 1220. A polyaxial hole 16 may be provided at the corners or ends of the cross member 1224. An additional polyaxial hole 16 may be provided along the length of the cross member 1224. The three holes 16 of the cross beam 1224 may be aligned in a straight line.

The rear extension 1226 may connect the main body 1212 to the planar offset extension 1222 and the cross member 1224. The rear extension 1226 may be a straight beam connecting the main body 1212 to the free end of the planar offset extension 1222. The rear extension 1226 may be aligned generally parallel to the posterior extension 1220. A series of polyaxial holes 16 defined through the rear extension 1216 may be aligned in a straight line. For example, a pair of holes 16 may be located toward the main body 1212 and another pair of holes 16 may be located with the plantar offset extension 1222.

The posterior section 1214, posterior extension 1220, cross member 1224, and rear extension 1226 of plate 1200 may form a generally rectangular outer shape. The planar offset extension 1222 may be a diagonal that divides the rectangle into two triangles with open space 1228 inside. The posterior section 1214 and posterior extension 1220 provide a row of rafting screw options below the subtalar joint, which may act as a raft to support subtalar joint fragments. The numerous screw options around the perimeter of implant 1200 target the cortical bone around the perimeter of the calcaneus, which improves structural stability. The screw holes 16 located on the inside and bottom of the plate 1200 provide additional points of fixation for the displaced fragments that may be displaced plantar. The rafting perimeter plates 1200 may be offered in small and large sizes as well as left and right configurations.

Figure 17A:
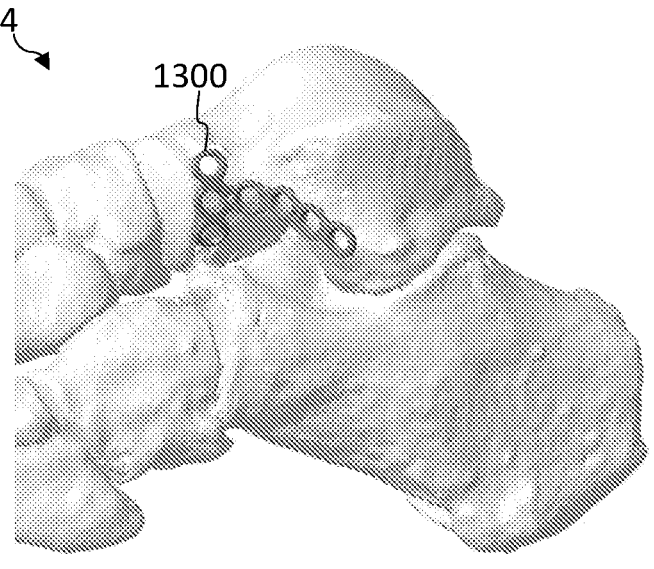
FIGS. 17A-17B depict a talus T-plate sitting laterally on the neck of the talus according to one embodiment.
Figure 17B:
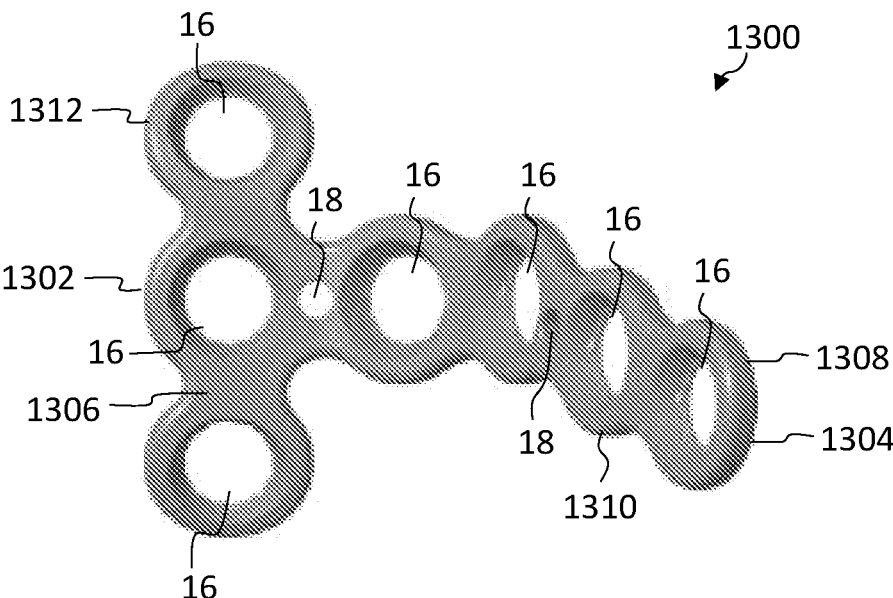

Turning now to FIGS. 17A-17B, a talus T-plate 1300 is shown according to one embodiment. As shown in FIG. 17A, the talus T-plates are contoured to sit laterally on the neck of the talus. Most fractures of the talus occur at the neck and plate 1300 is configured to provide fixation on the anterior and posterior fracture pieces. Turning now to FIG. 17B, the talus T-plate 1300 extends from a first anterior end 1302 configured to sit laterally on the neck of the talus to a second posterior end 1304 configured to sit laterally on the body of the talus. The plate 1300 includes a top surface 1306 and an opposite, bottom surface 1308 configured to contact adjacent bone.

The talus T-plates 1300 have a body with a substantially T-shaped profile. The T-plates 1300 have an elongate posterior portion or leg 1310 and a transverse anterior cross-portion 1312. The leg 1310 may be bent or angled relative to the cross-portion 1312. The posterior portion 1310 or leg of the T-shape may be contoured to mimic natural anatomy of the talus. The anterior portion 1312 or top of the T-shape may be contoured to wrap around the neck slightly. The transverse cross-portion 1312 may include one or more wings or extensions extending outwardly from the leg 1310. The cross-portion 1312 may be generally perpendicular to the leg 1310 of the plate 1300. The plate 1300 may include a plurality of polyaxial holes 16 and/or K-wire holes 18. The outer edges of the plate 1300 may be scalloped or wavy to follow the hole pattern, minimizing potential soft tissue irritation. The talus T-plates 1300 may be available in a variety of lengths along with a variety of hole options. The talus T-plates 1300 may be offered in both left and right configurations.

Figure 18A:
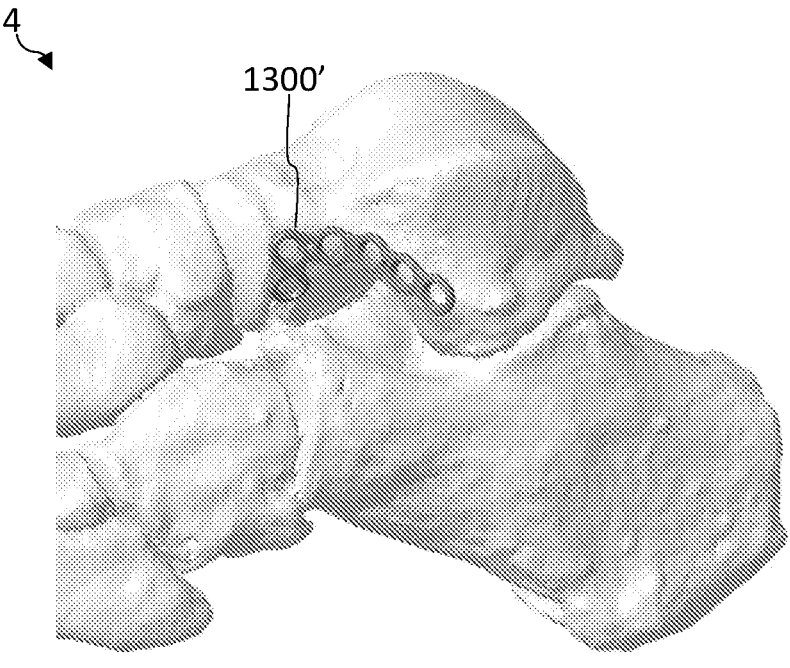
FIGS. 18A-18B depict a talus L-plate sitting laterally on the neck of the talus according to one embodiment.
Figure 18B:
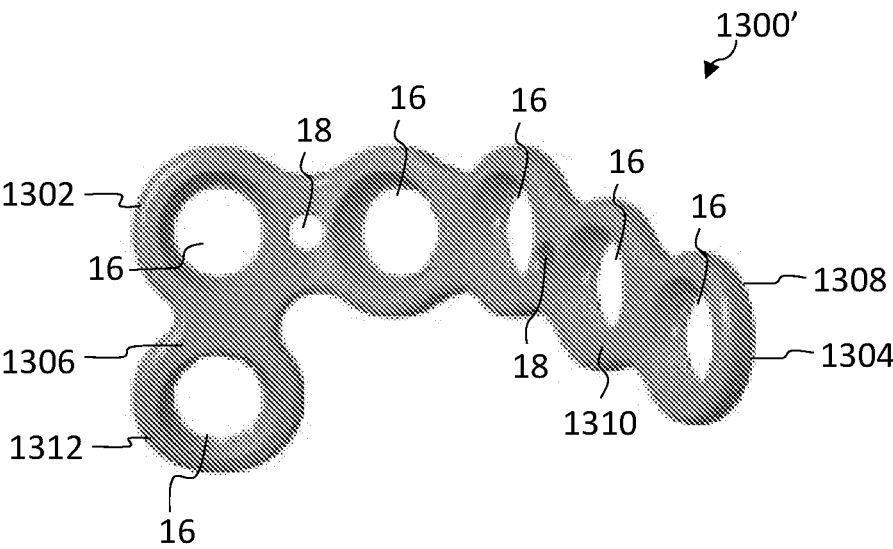

Turning now to FIGS. 18A-18B, a talus L-plate 1300' is shown according to one embodiment. The talus L-plate 1300' is the same as the talus T-plate except one wing or extension of the cross-portion 1312 has been removed. As shown in FIG. 18A, the talus L-plates 1300' are contoured to sit laterally on the neck of the talus. Like the talus T-plate 1300, the L-plate 1300' provides fixation on the anterior and posterior fracture pieces. FIG. 18B shows the talus L-plate 1300' with a substantially L-shaped profile. The L-plates 1300' offer one less screw hole anteriorly in cases where the additional fixation is not needed or when the T-plate 1300 is too large to fit the anatomy. The L-plates 1300' may be offered in both left and right configurations.

Figure 19A:
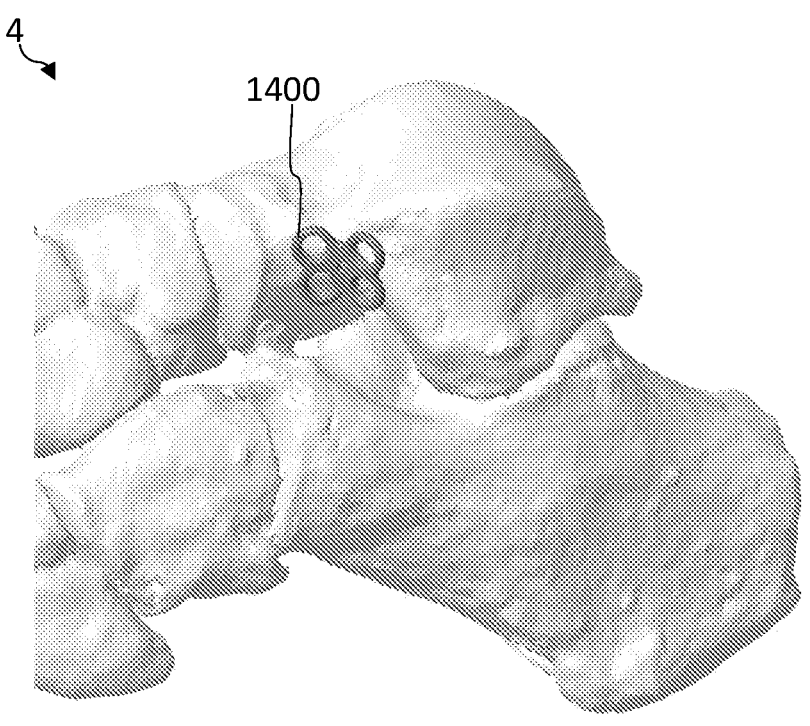
FIGS. 19A-19B depict a talus butterfly plate sitting laterally on the neck of the talus according to one embodiment.
Figure 19B:
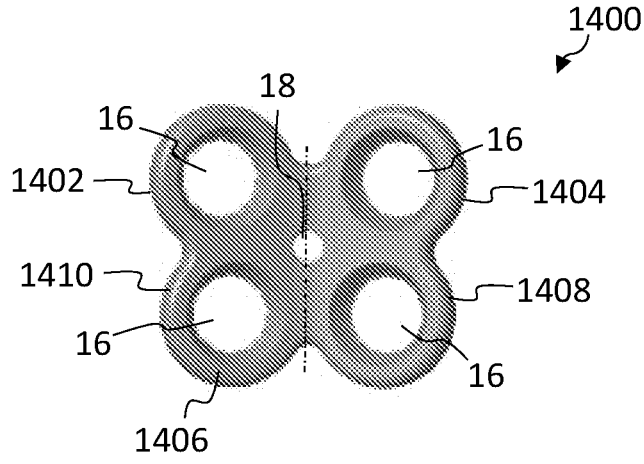

Turning now to FIGS. 19A-19B, a talus butterfly plate 1400 is shown according to one embodiment. As shown in FIG. 19A, the talus butterfly plates 1400 may be contoured to sit laterally on the neck of the talus. The talus butterfly plate 1400 is configured to provide fixation to the anterior and posterior fracture fragment pieces and provides two rows of screw holes for a more stable construct. As shown in FIG. 19B, the talus butterfly plate 1400 extends from a first anterior end 1402 configured to sit laterally on the neck of the talus to a second posterior end 1404 configured to sit laterally on the body of the talus. The plate 1400 includes a top surface 1406 and an opposite, bottom surface 1408 configured to contact adjacent bone.

Figure 20:
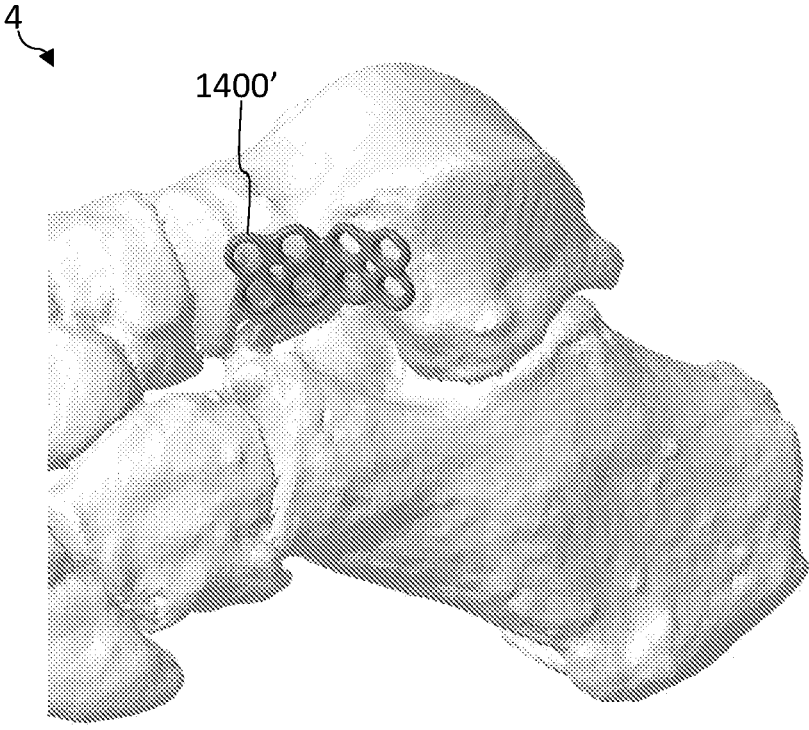
FIG. 20 depicts a large talus butterfly plate sitting laterally on the neck of the talus according to one embodiment.

The talus butterfly plate 1400 may have a symmetrical butterfly-like shape with opposed wings 1410. The wings 1410 may include lobes defining each polyaxial hole 16. For example, each wing 1410 may have an upper lobe and a lower lobe. The upper lobes may be slightly larger than the lower lobes. One wing 1410 with two holes 16 may be provided on the anterior end 1402 and a mirrored wing 1410 with two holes 16 may be provided on the posterior end 1404. The wings 1410 may be mirrored and bent about a center line. The outer edges of the plate 1400 may be scalloped or wavy to follow the outer hole pattern. A central K-wire hole 18 may be provided through the plate 1400. The talus butterfly plate 1400 may be offered in small and large configurations, which may be used on the left or right foot. As shown in FIG. 20, a large talus butterfly plate 1400' may extend the wings or lobes and provide four additional holes for fixation.

Figure 21:
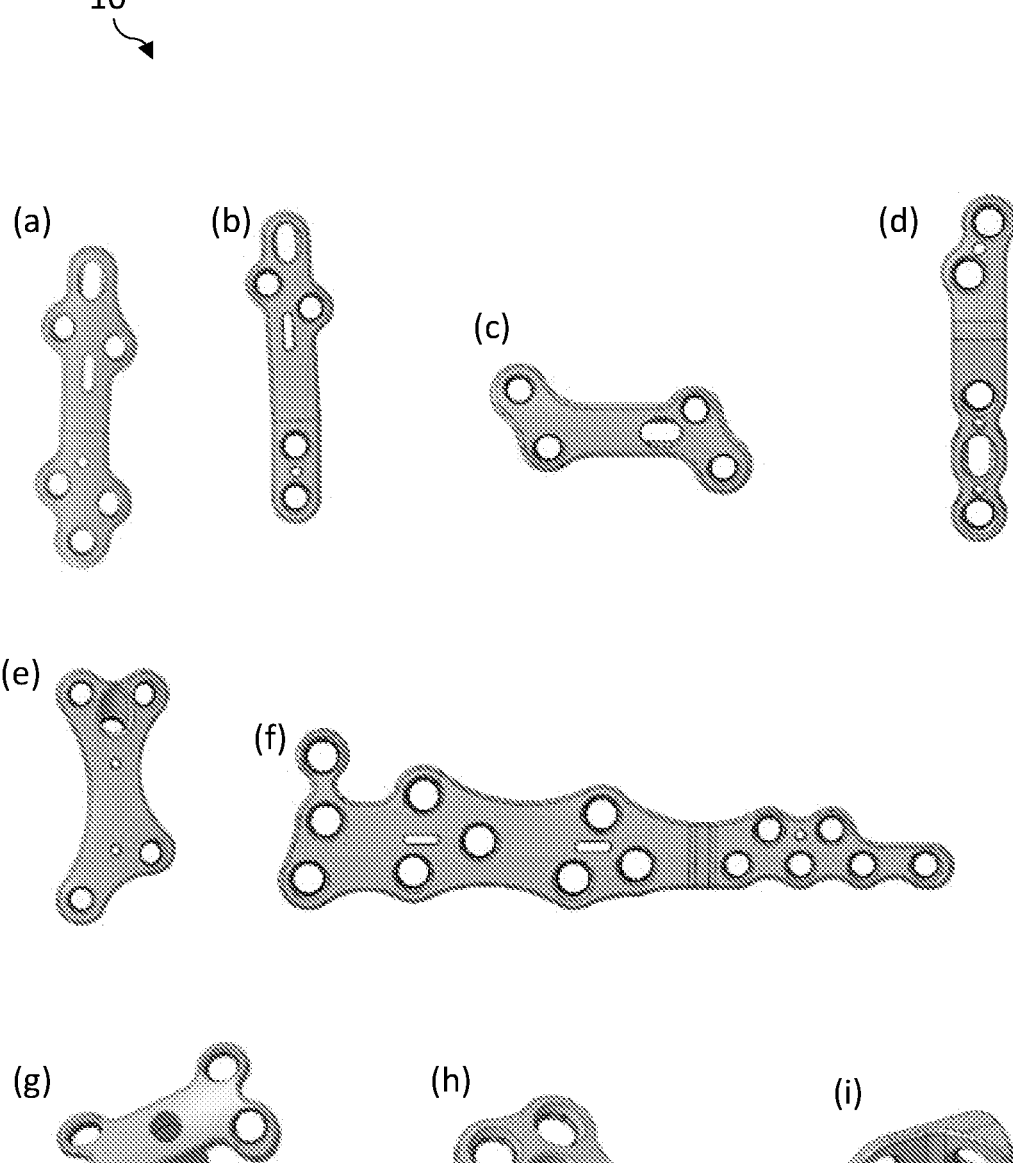
FIG. 21 shows a collection of reconstruction plate styles configured for fixating fractures of foot bones with complex fractures or complex three-dimensional geometry.

Turning now to FIG. 21, a series of reconstruction plates 10' may be used for fixation of bony anatomy after anatomic correction. The plates 10' may be used in the treatment of various fractures of the forefoot, midfoot, and hindfoot foot. Nine different plate styles in the treatment of various reconstructions include: (a) metatarsophalangeal (MTP) plates; (b) MTP low profile plates; (c) lapidus plates; (d) tarsometatarsal (TMT) plates; (e) navicular-cuneiform (NC) plates; (f) medial column plates; (g) Evans osteotomy wedge plates; (h) Cotton opening wedge plates; and (i) calcaneal slide plates.

Figure 22A:
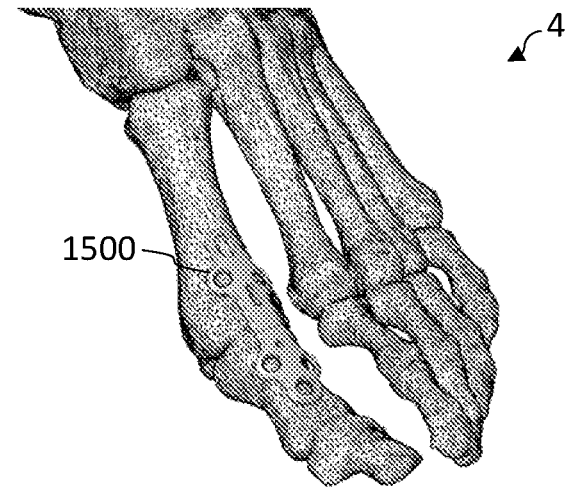
FIGS. 22A-22B depict a MTP plate sitting on the dorsal aspect of the metatarsophalangeal (MTP) joint according to one embodiment.
Figure 22B:
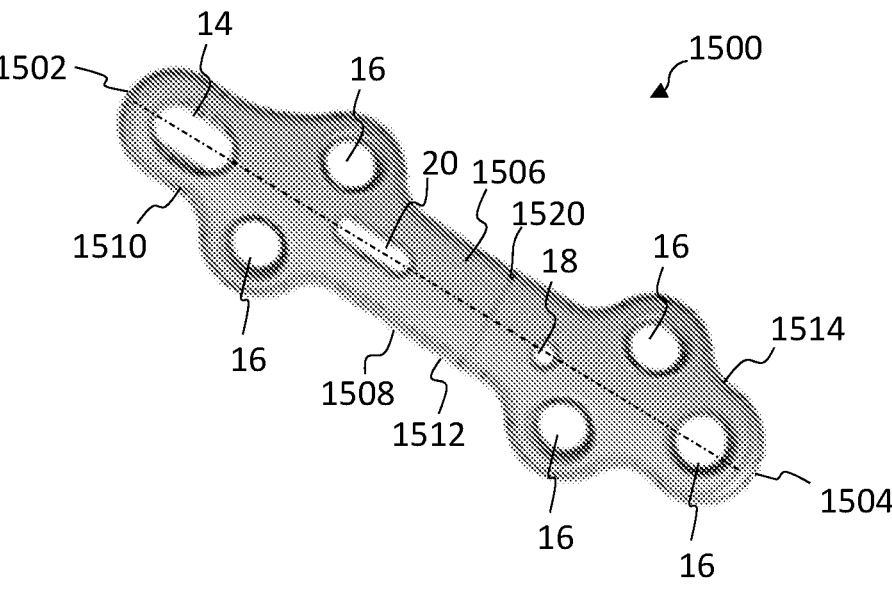

Turning now to FIGS. 22A-22B, a metatarsophalangeal (MTP) plate 1500 is shown according to one embodiment. As shown in FIG. 22A, the MTP plate 1500 is contoured to sit on the dorsal aspect of the first MTP joint. The MTP plate 1500 has a body that extends from a first end or proximal end 1502 configured to sit on the $1^{st}$ metatarsal to a second end or distal end 1504 configured to sit on the $1^{st}$ proximal phalanx. The plate 1500 includes a top surface 1506 and an opposite, bottom surface 1508 configured to contact adjacent bone. The plate 1500 may include three sections: proximal section 1510, bridge section 1512, and distal section 1514.

As shown in FIG. 22B, the proximal section 1510 defines at least two holes 16 proximally to fixate into the metatarsal. The proximal section 1510 further defines a compression hole 14 to achieve compression. The plate 1500 also defines a K-wire slot 20 to achieve further compression with a guide wire or K-wire. The bridge section 1512 may be a straight beam that extends over the MTP joint. The distal section 1514 defines three distal holes 16 to fixate into the phalanx. A K-wire hole 18 may also be provided distally. The compression slot 14, K-wire slot 20, K-wire hole 18, and distal-most polyaxial hole 16 may be aligned along the central longitudinal axis of the plate 1500. The outer edges of the proximal and distal sections 1510, 1514 may be scalloped or wavy to follow the hole pattern. The plate 1500 may include one or more markings 1520, indicators, cutouts, radiopaque markers, or the like, which indicate the general location of the joint. For example, a single line 1520 may show the position of the MTP joint across the top surface 1506 of the plate 1500. This marking 1520 may help the surgeon to optimally align the plate 1500 relative to the joint. The MTP plate 1500 may be left/right specific in small, medium, large, extra-large and revision options that offer more holes and longer bridge lengths in order to fit a larger section of the population.

Figure 23A:
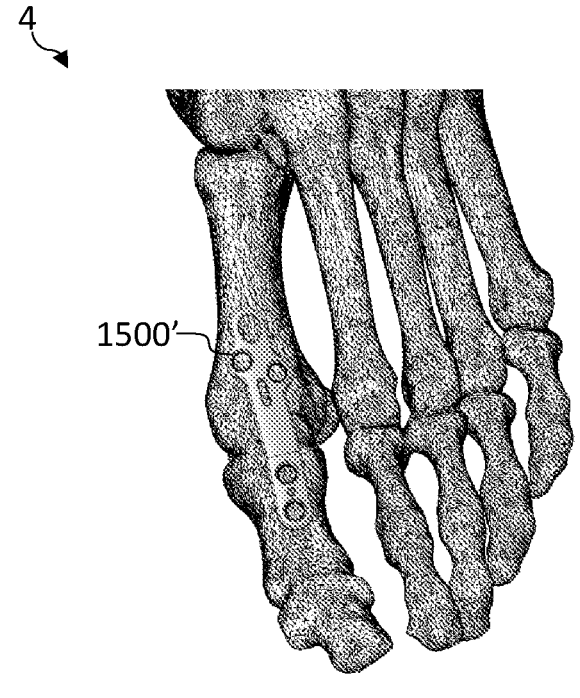
FIGS. 23A-23B depict a narrow MTP plate sitting on the dorsal aspect of the metatarsophalangeal (MTP) joint according to one embodiment.
Figure 23B:
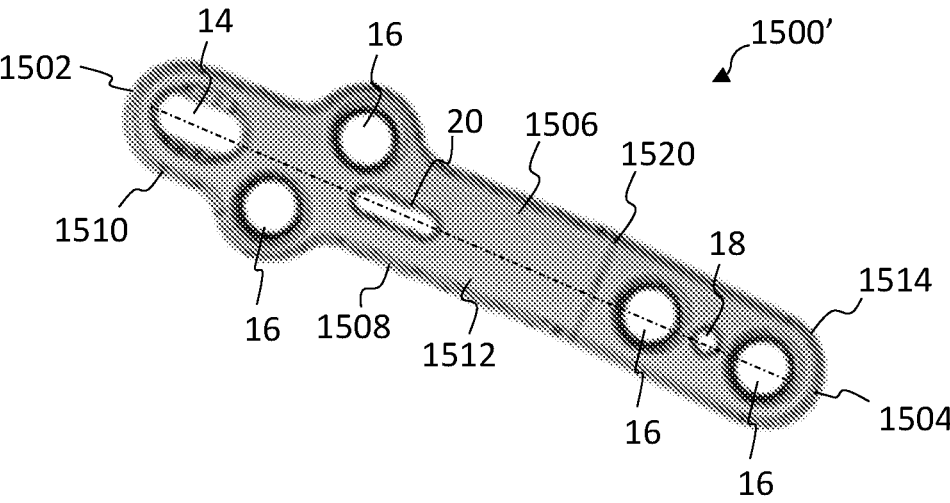

Turning now to FIGS. 23A-23B, a metatarsophalangeal (MTP) narrow plate 1500' is shown according to one embodiment. The MTP narrow plate 1500' is the same as the MTP plate 1500 except the plate is a slimmer version of the MTP plate that only has two screw holes distally for a lower profile on the phalanx. As shown in FIG. 23A, the MTP narrow plate 1500' is contoured to sit on the dorsal aspect of the first MTP joint. Similar to MTP plate 1500, the proximal end 1510 of the plate 1500' includes two polyaxially locking holes 16, one compression slot 14, and K-wire slot 20 to aid in compressing the joint. The distal end 1504 includes a straight extension off the bridge section 1512. The distal section 1514 defines two polyaxial locking holes 16 for securing into the phalanx. A K-wire hole 18 may be positioned between the distal holes 16. The width of the distal section 1514 may be the same as the bridge section 1512, thereby forming a narrow low profile.

Figure 24A:
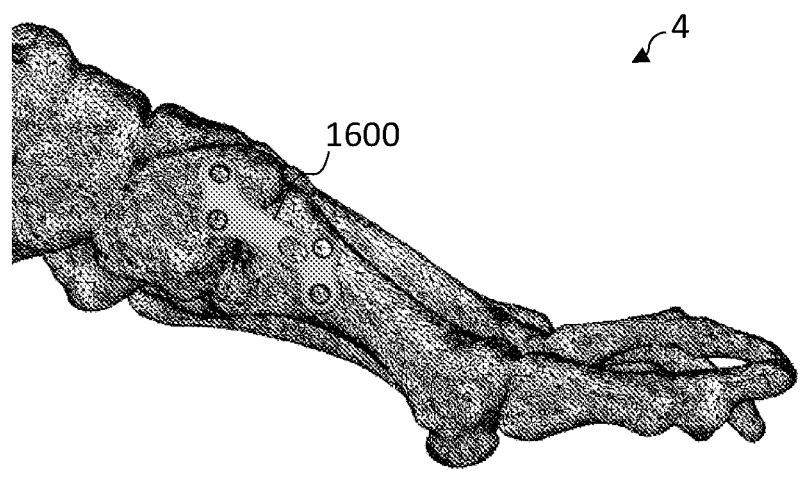
FIGS. 24A-24B depict a ladipus plate sitting on the medial aspect of the first metatarsal and medial cuneiform joint according to one embodiment.
Figure 24B:
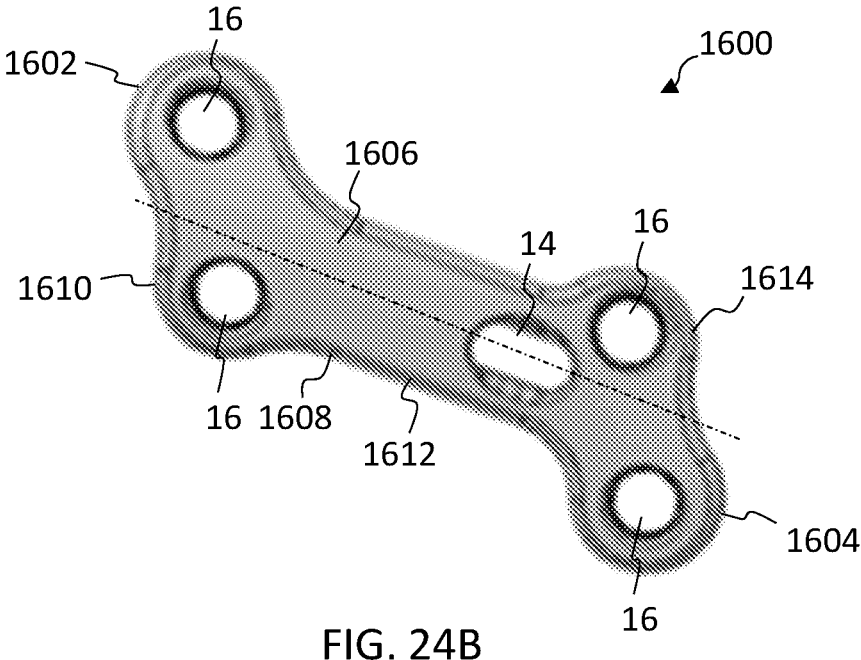

Turning now to FIGS. 24A-24B, a ladipus plate 1600 is shown according to one embodiment. As shown in FIG. 24A, the lapidus plate 1600 is contoured to sit on the medial aspect of the $1^{st}$ tarsometatarsal joint. The lapidus plate 1600 has a body that extends from a first end or proximal end 1602 configured to sit on the medial cuneiform to a second end or distal end 1604 configured to sit on the $1^{st}$ metatarsal. The plate 1600 includes a top surface 1606 and an opposite, bottom surface 1608 configured to contact adjacent bone. The plate 1600 may include three sections: proximal section 1610, bridge section 1612, and distal section 1614.

The proximal section 1610 includes polyaxial locking holes 16 configured to secure the plate 1600 to the medial cuneiform. The proximal section 1610 may include an upward projection or tab. The bridge section 1612 is angled or sloped downward toward the distal end 1604. The distal section 1614 includes polyaxial locking holes 16 configured to secure the plate 1600 to the first metatarsal. The distal section 1614 may include a downward projection or tab. A compression slot 14 may be provided along the sloped central axis of the plate 1600 toward the distal end 1604. In one embodiment, the lapidus plate 1600 includes four poly-axial locking holes 16, two for the metatarsal and two for the cuneiform, with one compression slot 14 on the side of the metatarsal. In another embodiment, a more robust plate offering may include six poly-axial holes 16 for receiving screws 12, with three in the metatarsal and three in the cuneiform. The plates 1600 may be left/right specific with short and long options where the bridge length changes proximally and distally.

Figure 25A:
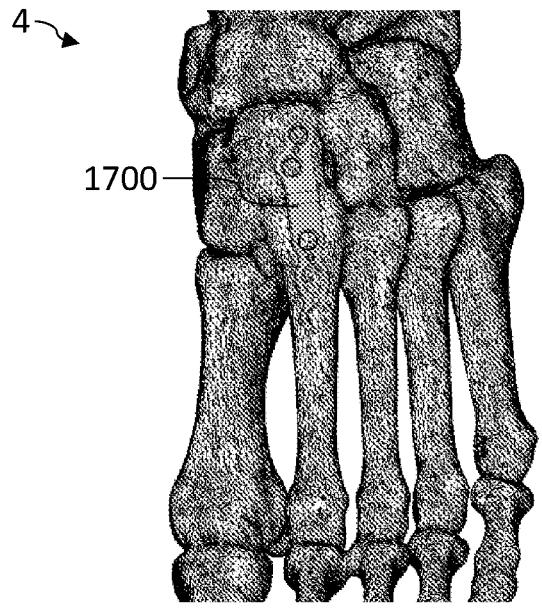
FIGS. 25A-25B depict a narrow TMT plate sitting on the dorsal aspect of the second tarsometatarsal joints (TMT) or Lisfranc joint according to one embodiment.
Figure 25B:
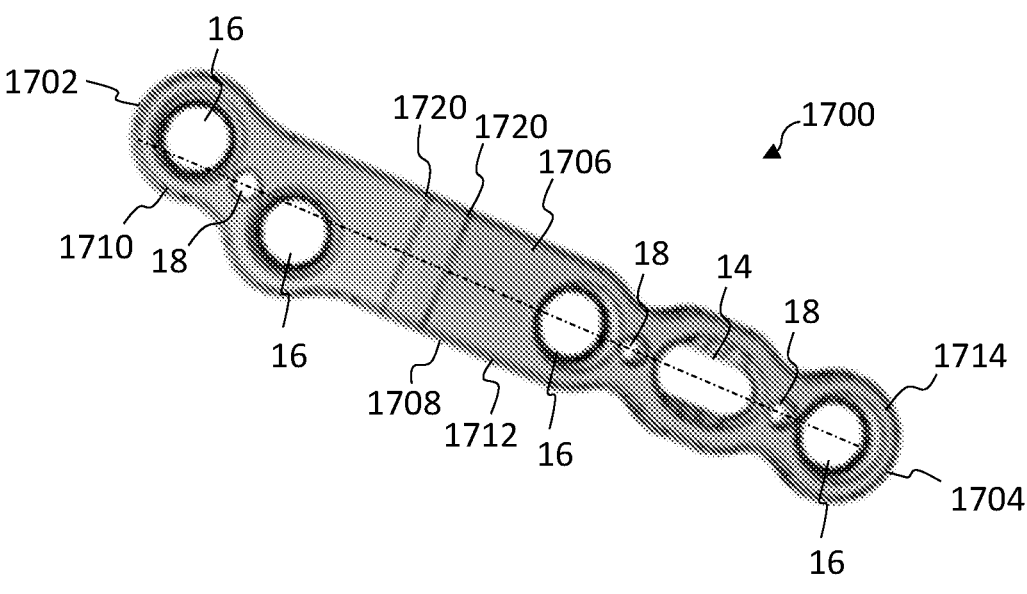

Turning now to FIGS. 25A-25B, a tarsometatarsal (TMT) plate 1700 is shown according to one embodiment. As shown in FIG. 25A, the TMT plate 1700 is contoured to sit dorsally on the second tarsometatarsal (TMT) joint. The TMT plate 1700 may be configured to fit the first, second, and third TMT joints or Lisfranc joints. The TMT plate 1700 has an elongate body that extends from a first end or proximal end 1702 configured to sit on the cuneiform to a second end or distal end 1704 configured to sit on the metatarsal. The plate 1700 includes a top surface 1706 and an opposite, bottom surface 1708 configured to contact adjacent bone. The plate 1700 may include three sections: proximal section 1710, bridge section 1712, and distal section 1714.

The proximal section 1710 or head of the plate 1700 may be provided in multiple screw-hole configurations, including T, L, oblique T, oblique L, and clover shapes in left and right orientations. In the embodiment shown, two polyaxial holes 16 are defined off-axis in the proximal section 1710 and a K-wire hole 18 is provided between them. The bridge section 1712 may be a straight solid beam spanning the TMT joint. The distal section 1714 may include two or four poly-axial holes 16 with a compression slot 14, thereby providing compression to the joint. The holes 16 and slot 14 may be aligned with the central longitudinal axis of the plate 1700. In the embodiment shown, the compression slot 14 is positioned between the holes 16 and two K-wire holes 18 are located between the slot 14 and adjacent holes 16. It will be appreciated that the plate 1700 may have any suitable arrangement of holes 16 for optimal attachment. The plate 1700 may include one or more markings 1720 or other indicators to show the general location of the joint. For example, a pair of parallel lines 1720 may show the position of the TMT joint across the top surface 1706 of the plate 1700. These markings 1720 may help the surgeon to optimally align the plate 1700 relative to the joint.

Figure 26:
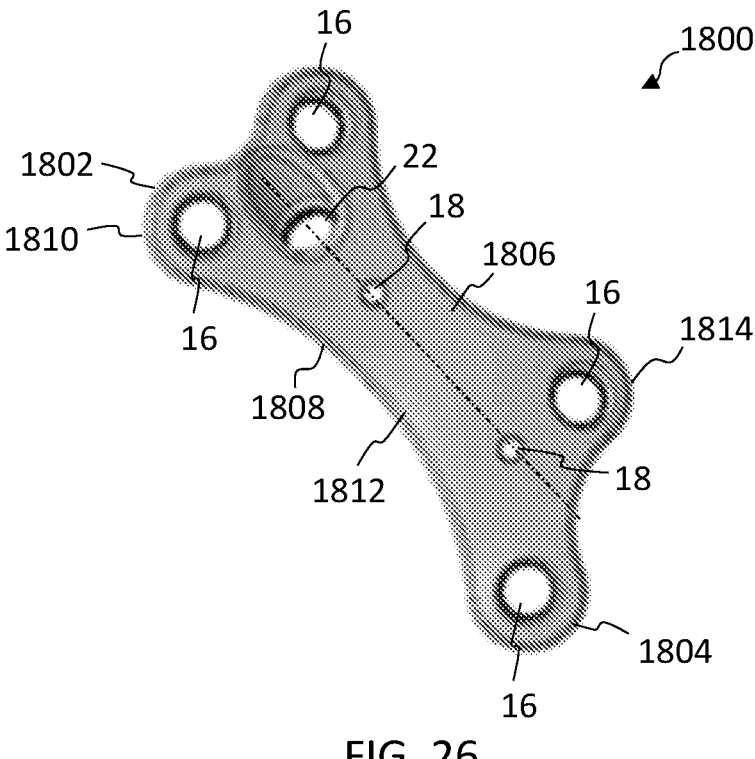
FIG. 26 depicts a NC fusion plate configured to sit dorsally over the navicular-cuneiform (NC) joint according to one embodiment.

Turning now to FIG. 26, a navicular-cuneiform (NC) plate 1800 is shown according to one embodiment. The NC fusion plate 1800 is contoured to sit dorsally over the navicular-cuneiform (NC) joint. The NC plate 1800 is configured to stabilize the medial and middle cuneiform to the navicular and also allow for an interfragmentary screw 12 to be sent through the plate 1800 through the use of a sunken hole 22.

The NC plate 1800 has an elongate body that extends from a first end or proximal end 1802 configured to sit on the navicular to a second end or distal end 1804 configured to sit on the cuneiform. The plate 1800 includes a top surface 1806 and an opposite, bottom surface 1808 configured to contact adjacent bone. The plate 1800 may include three sections: proximal section 1810, bridge section 1812, and distal section 1814.

The proximal section 1810 includes a pair of polyaxial locking holes 16 configured to secure the plate 1800 dorsally to the navicular. The proximal holes 16 may be located in lobes or ears at the proximal end 1802 of the plate 1800. The proximal section 1810 may further define sunken hole 22. The sunken hole 22 may be a polyaxial locking hole that acts as the near cortex for a lag screw. The sunken hole 22 may be located along the central axis of the plate 1800 but the hole axis may be angled such that the lag screw 12 inserts distally. The sunken hole 22 sits down into the plate 1800, and the surgeon may use a reamer to create a pocket in the bone for the plate 1800 to fit into.

The bridge section 1812 may include a solid section that is angled or sloped downward toward the distal end 1804. One or more K-wire holes 18 may be aligned along the central axis of the plate 1800. The distal section 1814 includes polyaxial locking holes 16 configured to secure the plate 1800 dorsally to the cuneiform. The distal holes 16 may be located in lobes or ears at the distal end 1804 of the plate 1800. One of the distal lobes may be elongated relative to the other lobes. The NC plates 1800 may be offered in both left and right configurations.

Figure 27A:
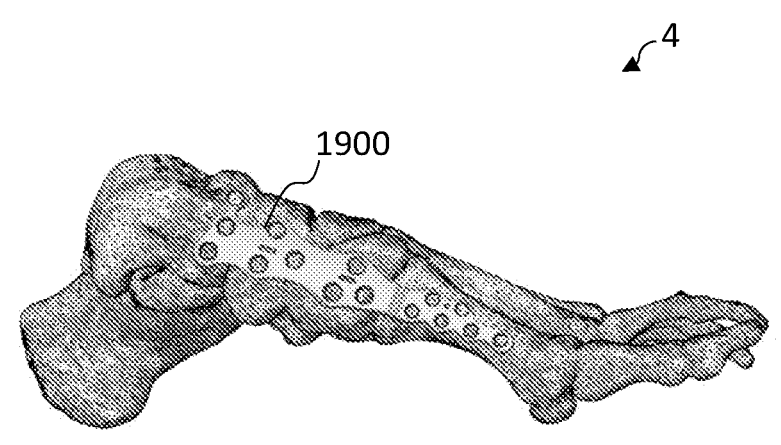
FIGS. 27A-27B depict a medial column plate spanning the medial aspect of the talus to first metatarsal according to one embodiment.
Figure 27B:
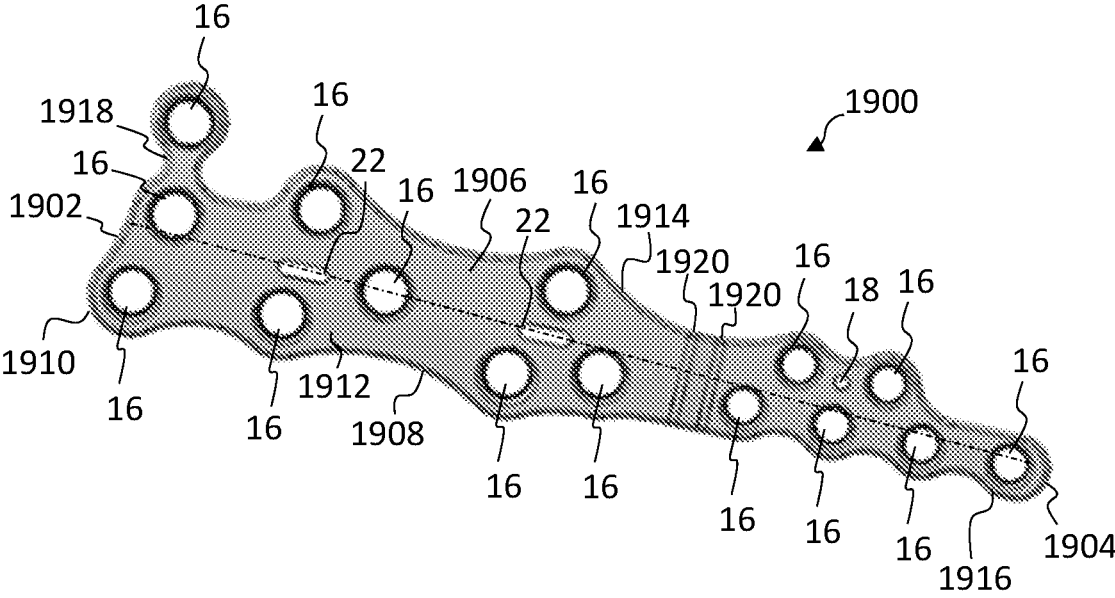

Turning now to FIGS. 27A-27B, a medial column plate 1900 is shown according to one embodiment. The medial column plate 1900 spans the medial aspect of the talus to the first metatarsal. As shown in FIG. 27A, the medial column plate 1900 is contoured to bridge across the midfoot covering the talus, navicular, medial cuneiform, and first metatarsal. The medial column plate 1900 allows for at least three screws to be placed in each of these bones while having a rigid structure to hold the bones in place.

The medial column plate 1900 has an elongate body that extends from a first end or proximal end 1902 configured to sit on the talus to a second end or distal end 1904 configured to sit on the metatarsal. The plate 1900 includes a top surface 1906 and an opposite, bottom surface 1908 configured to contact adjacent bone. The plate 1900 may include four sections: proximal talus section 1910, navicular section 1912, cuneiform section 1914, and distal metatarsal section 1916.

The proximal talus section 1910 includes three polyaxial holes 16 on the proximal-most end 1902 of the plate 1900 configured to secure screws 12 into the talus. One of the polyaxial holes 16 in the proximal talus section 1910 may protrude dorsally via tab 1918. The navicular section 1912 includes an arrangement of three polyaxial holes 16 configured to secure screws 12 into the navicular bone. The polyaxial holes 16 may be arranged in a triangular pattern with a first K-wire slot 22 configured to achieve compression with a guide wire or K-wire. The cuneiform section 1914 includes a triangular arrangement of three polyaxial holes 16 configured to secure screws 12 into the cuneiform with a second K-wire slot 22 for receiving a K-wire for further compression. The first and second K-wire slots 22 may be centrally located along the longitudinal axis of the plate 1900.

The distal metatarsal section 1916 includes a plurality of polyaxial holes 16 configured to secure screws 12 into the metatarsal. For example, six polyaxial holes 16 are arranged in two rows: two dorsally and four plantar. It will be appreciated, however, that any suitable arrangement of holes 16 may be used to secure the metatarsal. A K-wire hole 18 may be provided in the distal metatarsal section 1916 to offer guidance or additional point of fixation for the plate 1900. The plate 1900 may include one or more markings 1920 or other indicators to show the general location of the joint. For example, a pair of parallel stripes 1920 may show the position of the tarsometatarsal joint across the top surface 1906 of the plate 1900. These markings 1920 may help the surgeon to optimally align the plate 1900 relative to the tarsometatarsal joint. It will be appreciated that additional markings may be added for the other joints as well.

Figure 28A:
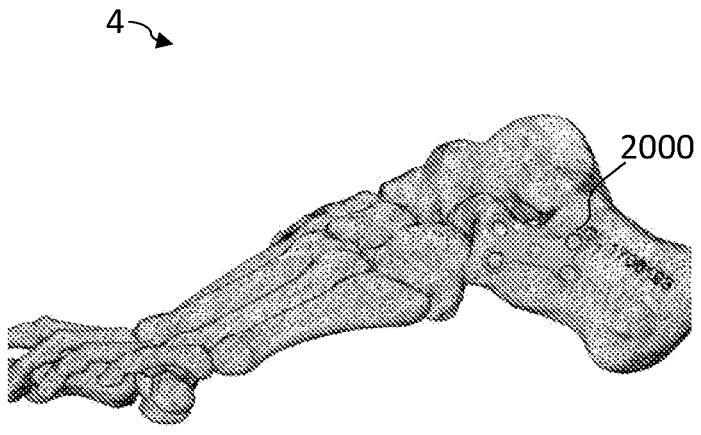
FIGS. 28A-28B depict an Evans osteotomy wedge plate sitting on the lateral aspect of the calcaneus over an osteotomy site according to one embodiment.
Figure 28B:
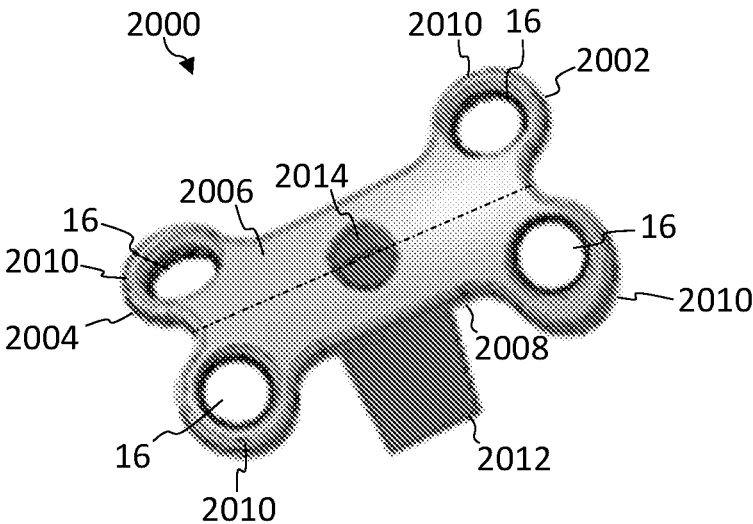

Turning now to FIGS. 28A-28B, an Evans osteotomy wedge plate 2000 is shown according to one embodiment. As best seen in FIG. 28A, the Evans osteotomy wedge plate 2000 is configured to fit into a calcaneal osteotomy. The Evans procedure may include creating an osteotomy on the lateral aspect of the calcaneus bone and inserting a wedge 2012 to lengthen the lateral column of the foot. The process of inserting the wedge 2012 fixes the valgus heel deformity by medializing the portion of the calcaneus posterior to the osteotomy. The plate portion sits over the osteotomy site and anchors the implant to the calcaneus.

As shown in FIG. 28B, the Evans osteotomy wedge plate 2000 extends from a first proximal end 2002 configured to sit proximal on the calcaneus to a second distal end 2004 configured to sit distal on the calcaneus. The plate 2000 includes a top surface 2006 and an opposite, bottom surface 2008 configured to contact adjacent bone. The plate 2000 may have symmetrical dog bone-like shape that is wider at both ends and narrower in the middle. The ends include lobes 2010 each defining one polyaxial hole 16. The lobes 2010 may be bent or contoured to mimic the shape of the calcaneus. The outer edges of the lobes 2010 may be rounded to follow the hole pattern. A static wedge 2012 protrudes from the bottom surface 2008 and is configured to fit within an osteotomy cut into the calcaneus. The wedge 2012 includes one or more inclined planes or surfaces configured to spread the bone at an angle. The plate 2000 may then be fixated with two polyaxial screws 12 on either side of the osteotomy. The plate 2000 may include a bone graft window 2014, for example, through the face of the plate 2000 and into the wedge 2012, that can be filled pre- or post-implantation.

Figure 29A:
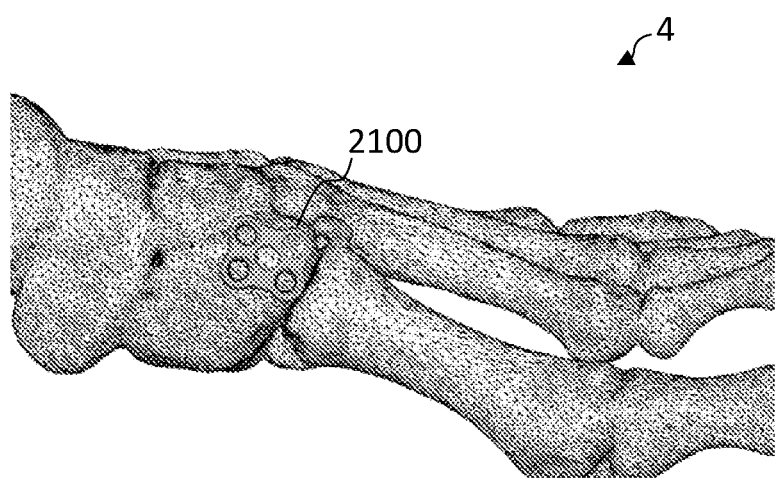
FIGS. 29A-29B depict a Cotton opening wedge plate sitting on the dorsomedial aspect of the medial cuneiform according to one embodiment.
Figure 29B:
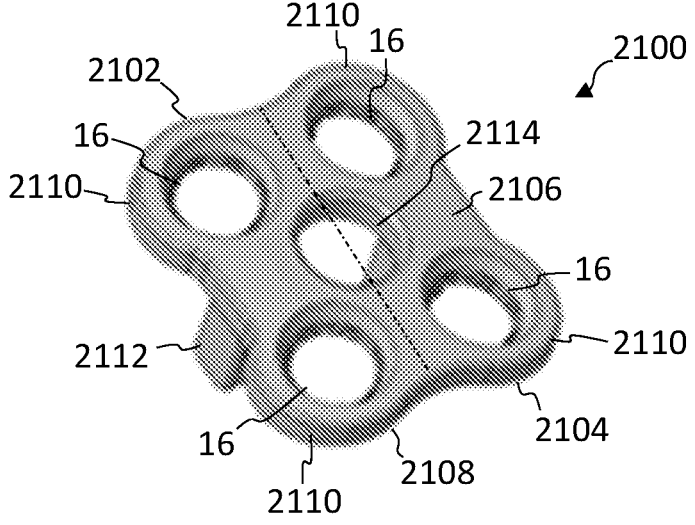

Turning now to FIGS. 29A-29B, a Cotton opening wedge plate 2100 is shown according to one embodiment. As best seen in FIG. 29A, the Cotton opening wedge plate 2100 is configured to fit into a medial cuneiform osteotomy. The Cotton procedure may include creating an osteotomy on the medial aspect of the cunieform bone and inserting a wedge 2112 to lengthen the top of the medial cuneiform, creating an arch in the foot. The procedure is commonly performed to help correct the condition of pes planus or flat foot. The plate portion sits on the dorsomedial aspect of the medial cuneiform over the osteotomy site and anchors the implant to the cunieform.

As shown in FIG. 29B, the Cotton opening wedge plate 2100 extends from a first proximal end 2102 configured to sit proximal on the cunieform to a second distal end 2104 configured to sit distal on the cunieform. The plate 2100 includes a top surface 2106 and an opposite, bottom surface 2108 configured to contact adjacent bone. The plate 2100 may have symmetrical shape with lobes 2110 at the four corners each defining one polyaxial hole 16. The plate 2100 may be substantially flat or planar. The outer edges of the lobes 2110 may be rounded or contoured to follow the hole pattern. A static wedge 2112 protrudes from the bottom surface 2108 and is configured to fit within an osteotomy cut into the cunieform. The wedge 2112 includes one or more inclined planes or surfaces configured to spread the bone at an angle. The plate 2100 may then be fixated with two polyaxial screws 12 on either side of the osteotomy. The plate 2100 may include a central bone graft window 2114, for example, through the face of the plate 2100 and into the wedge 2112, that can be filled pre- or post-implantation.

Figure 30A:
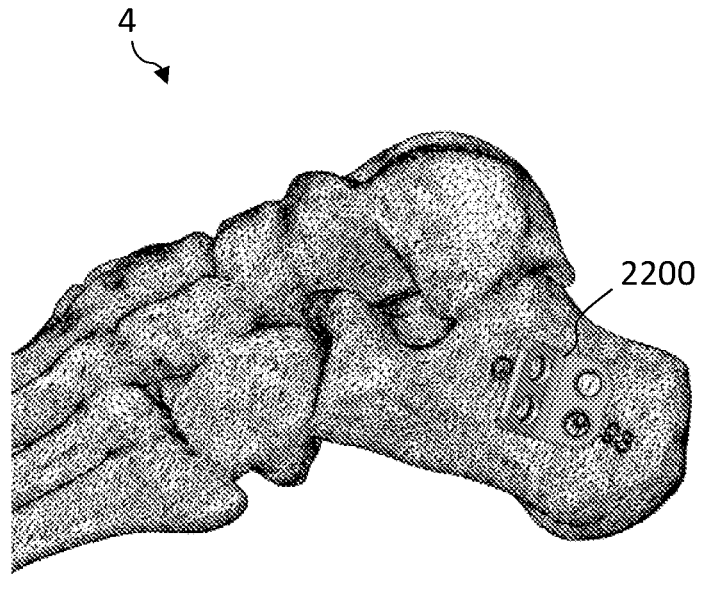
FIGS. 30A-30B depict a calcaneal slide plate sitting on the lateral aspect of the calcaneus osteotomy site according to one embodiment.
Figure 30B:
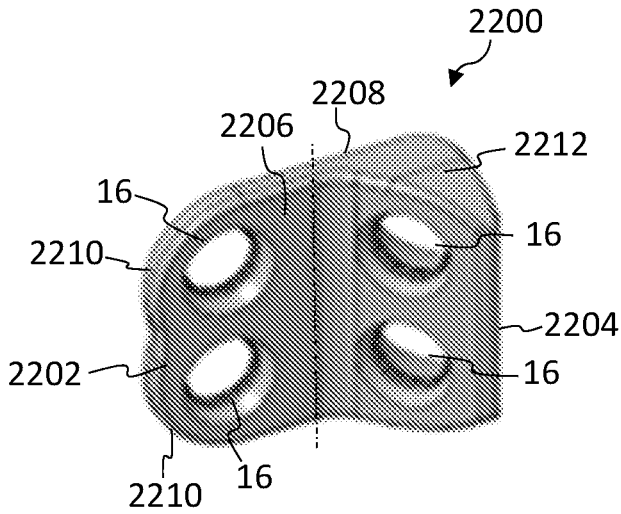

Turning now to FIGS. 30A-30B, a calcaneal slide plate 2200 is shown according to one embodiment. As best seen in FIG. 30A, the calcaneal slide plate 2200 is sitting on a lateral aspect of a calcaneus osteotomy site. The calcaneal slide plate 2200 is configured to fixate the calcaneus osteotomy after it has been translated to correct a deformity. A calcaneal sliding osteotomy changes the alignment of the calcaneus or heel bone. The procedure involves cutting the calcaneus, adjusting or shifting the rear portion of the bone, and stabilizing the bone with the implant. The calcaneal sliding osteotomy may be used to correct problems, such as flat foot or an abnormally high arch.

As shown in FIG. 30B, the calcaneal slide plate 2200 extends from a first proximal end 2202 configured to sit proximal on the calcaneus to a second distal end 2104 configured to sit distal on the calcaneus. The plate 2200 includes a top surface 2206 and an opposite, bottom surface 2208 configured to contact adjacent bone. The plate 2200 may include a plate portion with lobes 2210 defining polyaxial holes 16 and a wedge portion 2212 defining polyaxial holes 16. The plate portion and wedge portion 2212 may be bent or angled relative to one another. The wedge portion 2212 may include one or more inclined planes or surfaces. The wedge portion 2212 may be configured to protrude laterally. The plates 2200 may come in multiple different sizes, which account for the correction of the slide based on the height of the implant. The plate 2200 allows for two polyaxial screws 12 to be placed on either side of the osteotomy. The screws 12 secure the two halves of the calcaneus so that it may heal into the corrected position.

The collection of foot plates 10 include a comprehensive offering to treat a vast array of fracture patterns in the forefoot, midfoot, and hindfoot. The plates 10 may be used for both definitive, permanent fixation, as well as temporary or supplemental fixation in accordance with other systems. The specific plate styles afford the ability to accommodate multiple fracture patterns. The plates are capable of being cut and contoured to accommodate extreme patient anatomy. The large range of screw and plate sizes can accommodate multiple anatomies and anatomic regions.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. A bone stabilization plate comprising:
   an elongate body having a longitudinal axis, a top surface and an opposite, bottom surface configured to contact bone, the elongate body having a first section, a main body, and a second section, and the elongate body defines a plurality of screw holes therethrough, wherein the first section is offset from the main body with two tabs, the main body includes a three-hole polyaxial cluster where an axis of each hole is located at vertices of an equilateral triangle, and the second section includes a series of at least three polyaxial holes following a wave pattern extending along the longitudinal axis, wherein each tab extends from one hole of the three-hole poly axial cluster, and wherein the first section, the two tabs, and the main body are disposed relative to each other in a manner to create an enclosed interspace between the first section and the main body, wherein the elongate body includes a posterior extension including a straight continuation of the second section, wherein the posterior extension includes a linear arrangement of polyaxial holes, wherein the elongate body includes a plantar offset extension extending from the second section, wherein the plantar offset extension includes a second straight continuation of the second section angled relative to the posterior extension, wherein the plantar offset extension includes a solid linear body that terminates with a three-hole cluster, wherein the plantar offset extension is connected to the posterior extension by a cross member, and the main body is connected to the planar offset extension by a rear extension.

2. The plate of claim 1, wherein the plate is contoured to sit laterally on a calcaneus below a talus.

3. The plate of claim 1, wherein the two tabs are angled inward and toward one another toward the main body.

4. The plate of claim 1, wherein the elongate body defines a k-wire hole having a diameter smaller than a diameter of each of the screw holes.

\* \* \* \* \*